(12) United States Patent
Piergallini et al.

(10) Patent No.: US 11,331,257 B2
(45) Date of Patent: May 17, 2022

(54) BIOPHOTONIC COMPOSITIONS AND METHODS FOR PROVIDING BIOPHOTONIC TREATMENT

(71) Applicant: KLOX TECHNOLOGIES INC., Laval (CA)

(72) Inventors: Remigio Piergallini, San Benedetto del Tronto (IT); Nikolaos Loupis, Athens (GR); Shipra Rastogi, Montreal (CA)

(73) Assignee: KLOX TECHNOLOGIES INC., Laval (CA)

( * ) Notice: Subject to any disclaimer, the term of this patent is extended or adjusted under 35 U.S.C. 154(b) by 228 days.

(21) Appl. No.: 16/536,996

(22) Filed: Aug. 9, 2019

(65) Prior Publication Data

US 2019/0358142 A1 Nov. 28, 2019

Related U.S. Application Data

(63) Continuation of application No. 15/201,111, filed on Jul. 1, 2016, now Pat. No. 10,376,455, which is a continuation of application No. 13/830,488, filed on Mar. 14, 2013, now abandoned.

(60) Provisional application No. 61/766,611, filed on Feb. 19, 2013, provisional application No. 61/701,513, filed on Sep. 14, 2012, provisional application No. 61/701,510, filed on Sep. 14, 2012, provisional application No. 61/701,502, filed on Sep. 14, 2012, provisional application No. 61/636,574, filed on Apr. 20, 2012, provisional application No. 61/636,577, filed on Apr. 20, 2012, provisional application No. 61/636,480, filed on Apr. 20, 2012.

(51) Int. Cl.
| | | |
|---|---|---|
| *A61K 8/49* | (2006.01) | |
| *A61N 5/06* | (2006.01) | |
| *A61Q 19/00* | (2006.01) | |
| *A61K 8/04* | (2006.01) | |
| *A61K 8/22* | (2006.01) | |
| *A61Q 19/08* | (2006.01) | |
| *A61K 41/00* | (2020.01) | |
| *A61K 8/81* | (2006.01) | |
| *A61Q 19/02* | (2006.01) | |

(52) U.S. Cl.
CPC ............. *A61K 8/498* (2013.01); *A61K 8/042* (2013.01); *A61K 8/22* (2013.01); *A61K 8/8147* (2013.01); *A61K 41/00* (2013.01); *A61K 41/0057* (2013.01); *A61N 5/06* (2013.01); *A61N 5/062* (2013.01); *A61N 5/0616* (2013.01); *A61Q 19/00* (2013.01); *A61Q 19/02* (2013.01); *A61Q 19/08* (2013.01); *A61K 2800/262* (2013.01); *A61K 2800/434* (2013.01); *A61K 2800/5922* (2013.01); *A61K 2800/81* (2013.01); *A61N 2005/0645* (2013.01); *A61N 2005/0647* (2013.01); *A61N 2005/0662* (2013.01); *A61N 2005/0663* (2013.01)

(58) Field of Classification Search
CPC .. A61K 41/00; A61K 41/008; A61K 41/0042; A61K 41/0057; A61K 8/22; A61K 8/36; A61K 8/042; A61K 8/60; A61K 8/97; A61K 8/492; A61K 8/494; A61K 8/498; A61K 8/602735; A61K 2800/81; A61K 2800/262; A61K 2800/434; A61K 2800/5922; A61Q 19/00; A61Q 19/08; A61N 5/06; A61N 5/062; A61N 5/0616; A61N 5/0624; A51N 2005/0662; A51N 2005/0606; A51N 2005/0644
See application file for complete search history.

(56) References Cited

U.S. PATENT DOCUMENTS

| | | |
|---|---|---|
| 2,877,221 A | 3/1959 | Lanbach |
| 3,141,321 A | 7/1964 | Rinaldi |
| 3,293,127 A | 12/1966 | Beck |
| 3,309,274 A | 3/1967 | Brilliant |
| 3,372,125 A | 3/1968 | Hill |
| 3,595,798 A | 7/1971 | Smith et al. |
| 3,597,362 A | 8/1971 | Rauhut et al. |
| 3,652,420 A | 3/1972 | Hill |
| 3,671,450 A | 6/1972 | Rauhut et al. |
| 3,728,446 A | 4/1973 | Roberts et al. |
| 4,320,140 A | 3/1982 | Crounse et al. |
| 4,402,959 A | 9/1983 | Dybas et al. |
| 4,430,381 A | 2/1984 | Harvey et al. |
| 4,518,578 A | 5/1985 | Hayes et al. |
| 4,533,435 A | 8/1985 | Intili |
| 4,574,097 A | 3/1986 | Honeycutt |

(Continued)

FOREIGN PATENT DOCUMENTS

| | | |
|---|---|---|
| CA | 2222027 A1 | 6/1998 |
| CA | 2360202 A1 | 7/2000 |

(Continued)

OTHER PUBLICATIONS

English abstract for JP 2008-510829 provided.
(Continued)

*Primary Examiner* — Boniface Ngathi N.
(74) *Attorney, Agent, or Firm* — BCF LLP

(57) ABSTRACT

The present disclosure provides biophotonic topical compositions and methods useful in phototherapy. In particular, the biophotonic topical compositions of the present disclosure are substantially resistant to leaching such that very low amounts of chromophore(s) present in the biophotonic composition leach out of the composition. The biophotonic compositions and the methods of the present disclosure are useful for promoting wound healing and skin rejuvenation, as well as treating acne and various skin disorders.

19 Claims, 19 Drawing Sheets

(56) References Cited

U.S. PATENT DOCUMENTS

| | | |
|---|---|---|
| 4,625,026 A | 11/1986 | Kim |
| 4,736,467 A | 4/1988 | Schwarze et al. |
| 4,846,165 A | 7/1989 | Hare et al. |
| 4,855,139 A | 8/1989 | Srinivasan |
| 4,891,211 A | 1/1990 | Winston |
| 4,992,256 A | 2/1991 | Skaggs et al. |
| 5,069,907 A | 12/1991 | Mixon et al. |
| 5,091,102 A | 2/1992 | Sheridan |
| 5,292,362 A | 3/1994 | Bass et al. |
| 5,354,790 A | 10/1994 | Keusch et al. |
| 5,529,769 A | 6/1996 | Cho et al. |
| 5,611,793 A | 3/1997 | Wilson et al. |
| 5,639,464 A | 6/1997 | Terry et al. |
| 5,658,148 A | 8/1997 | Neuberger et al. |
| 5,723,148 A | 3/1998 | Love |
| 5,749,968 A | 5/1998 | Melanson et al. |
| 5,785,527 A | 7/1998 | Jensen et al. |
| 5,844,016 A | 12/1998 | Sawhney et al. |
| 5,853,883 A | 12/1998 | Nohr et al. |
| 5,854,147 A | 12/1998 | Nohr et al. |
| 5,858,332 A | 1/1999 | Jensen et al. |
| 5,894,042 A | 4/1999 | Ferralli |
| 5,919,554 A | 7/1999 | Watterson et al. |
| 5,922,331 A | 7/1999 | Mausner |
| 5,977,199 A | 11/1999 | Xie |
| 6,030,222 A | 2/2000 | Tarver |
| 6,036,493 A | 3/2000 | Sharma |
| 6,056,548 A | 5/2000 | Neuberger et al. |
| 6,084,005 A | 7/2000 | Fukunishi et al. |
| 6,107,466 A | 8/2000 | Hasan et al. |
| 6,121,341 A | 9/2000 | Sawhney et al. |
| 6,149,895 A | 11/2000 | Kutsch |
| 6,162,055 A | 12/2000 | Montgomery et al. |
| 6,203,805 B1 | 3/2001 | Collins et al. |
| 6,254,388 B1 | 7/2001 | Yarborough |
| 6,267,976 B1 | 7/2001 | Barnhart et al. |
| 6,337,357 B1 | 1/2002 | Fukunishi et al. |
| 6,343,933 B1 | 2/2002 | Montgomery et al. |
| 6,361,329 B1 | 3/2002 | Dekker et al. |
| 6,365,134 B1 | 4/2002 | Orlowski et al. |
| 6,387,353 B1 | 5/2002 | Jensen et al. |
| 6,391,283 B1 | 5/2002 | Jensen et al. |
| 6,420,455 B1 | 7/2002 | Landgrebe et al. |
| 6,423,697 B1 | 7/2002 | Friedman |
| 6,440,396 B1 | 8/2002 | McLaughlin |
| 6,444,725 B1 | 9/2002 | Trom et al. |
| 6,475,497 B1 | 11/2002 | Rajaiah et al. |
| 6,485,709 B2 | 11/2002 | Banerjee et al. |
| 6,488,914 B2 | 12/2002 | Montgomery |
| 6,514,543 B2 | 2/2003 | Montgomery |
| 6,528,555 B1 | 3/2003 | Nikutowski et al. |
| 6,536,628 B2 | 3/2003 | Montgomery |
| 6,541,460 B2 | 4/2003 | Petito |
| 6,558,653 B2 | 5/2003 | Andersen |
| 6,846,182 B1 | 1/2005 | Sibnef |
| 6,905,672 B2 | 6/2005 | Rajaiah et al. |
| 6,960,079 B2 | 11/2005 | Brennan et al. |
| 7,066,941 B2 | 6/2006 | Perricone |
| 7,081,128 B2 | 7/2006 | Hart et al. |
| 7,083,610 B1 | 8/2006 | Murray |
| 7,114,953 B1 | 10/2006 | Wagner |
| 7,220,438 B2 | 5/2007 | Quintanilla Almagro et al. |
| 7,314,470 B2 | 1/2008 | Malodobry |
| 7,354,448 B2 | 4/2008 | Altshuler et al. |
| 7,598,291 B2 | 10/2009 | Nimni et al. |
| 7,722,904 B2 | 5/2010 | Schneider et al. |
| 8,075,875 B2 | 12/2011 | Piergallini et al. |
| 8,182,473 B2 | 5/2012 | Altshuler et al. |
| 8,334,328 B2 | 12/2012 | Marmarinos et al. |
| 8,414,911 B2 | 4/2013 | Mattson et al. |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,911,791 B2 | 12/2014 | Piergallini et al. |
| 8,974,833 B2 | 3/2015 | Piergallini et al. |
| 8,986,719 B2 | 3/2015 | Piergallini et al. |
| 8,986,745 B2 | 3/2015 | Piergallini et al. |
| 8,986,746 B2 | 3/2015 | Piergallini et al. |
| 9,375,446 B2 | 6/2016 | Piergallini et al. |
| 2001/0022970 A1 | 9/2001 | Dees et al. |
| 2002/0197214 A1 | 12/2002 | Bublewitz et al. |
| 2003/0133940 A1 | 7/2003 | Dees et al. |
| 2003/0134932 A1 | 7/2003 | Lehmann et al. |
| 2003/0162760 A1 | 8/2003 | Masatsuji et al. |
| 2003/0167964 A1 | 9/2003 | Anderson et al. |
| 2003/0198605 A1 | 10/2003 | Montgomery |
| 2004/0009227 A1 | 1/2004 | Yao |
| 2004/0028624 A1 | 2/2004 | Bublewitz et al. |
| 2004/0097627 A1 | 5/2004 | Vallittu et al. |
| 2004/0136971 A1 | 7/2004 | Scharp et al. |
| 2004/0191330 A1 | 9/2004 | Keefe et al. |
| 2004/0193235 A1 | 9/2004 | Altshuler et al. |
| 2004/0258723 A1 | 12/2004 | Singh et al. |
| 2004/0262569 A1 | 12/2004 | Cho et al. |
| 2005/0020696 A1 | 1/2005 | Montgomery et al. |
| 2005/0026298 A1 | 2/2005 | Bickett et al. |
| 2005/0042712 A1 | 2/2005 | Huth et al. |
| 2005/0049228 A1 | 3/2005 | Albrecht et al. |
| 2005/0059731 A1 | 3/2005 | Albrecht et al. |
| 2005/0080465 A1 | 4/2005 | Zelickson et al. |
| 2005/0098766 A1 | 5/2005 | Watson |
| 2005/0100514 A1 | 5/2005 | Sakaguchi et al. |
| 2005/0123588 A1 | 6/2005 | Zhu et al. |
| 2005/0124721 A1 | 6/2005 | Arthur et al. |
| 2005/0124722 A1 | 6/2005 | Arthur et al. |
| 2005/0249677 A1 | 11/2005 | Malcmacher et al. |
| 2006/0099155 A1 | 5/2006 | MacDonald et al. |
| 2006/0198796 A1 | 9/2006 | Giniger et al. |
| 2006/0217690 A1 | 9/2006 | Bastin et al. |
| 2006/0228320 A1 | 10/2006 | Minami |
| 2006/0237696 A1 | 10/2006 | Gourlaouen et al. |
| 2006/0247313 A1 | 11/2006 | Murakami et al. |
| 2006/0251687 A1 | 11/2006 | Lapidot et al. |
| 2006/0287211 A1 | 12/2006 | Barbizan et al. |
| 2007/0092469 A1 | 4/2007 | Jacobs |
| 2007/0128132 A1 | 6/2007 | Piergallini et al. |
| 2007/0142762 A1 | 6/2007 | Kaplan |
| 2007/0148623 A1 | 6/2007 | Dias et al. |
| 2007/0166369 A1 | 7/2007 | Neuberger et al. |
| 2007/0191249 A1 | 8/2007 | Lant |
| 2007/0244195 A1 | 10/2007 | Burkhart et al. |
| 2007/0286824 A1 | 12/2007 | Rabe et al. |
| 2008/0058689 A1 | 3/2008 | Holloway et al. |
| 2008/0108681 A1 | 5/2008 | Scimeca et al. |
| 2008/0113037 A1 | 5/2008 | Green et al. |
| 2008/0138289 A1 | 6/2008 | Goronkin |
| 2008/0206159 A1 | 8/2008 | Tamarkin et al. |
| 2008/0305101 A1 | 12/2008 | Ruoslahti et al. |
| 2009/0131499 A1 | 2/2009 | Castro et al. |
| 2009/0060856 A1 | 3/2009 | Katsuyama et al. |
| 2009/0069217 A1 | 3/2009 | Kato et al. |
| 2009/0130030 A1 | 5/2009 | Ribi |
| 2009/0220450 A1 | 9/2009 | Green et al. |
| 2009/0238778 A1 | 9/2009 | Mordas et al. |
| 2009/0269121 A1 | 10/2009 | Snedden et al. |
| 2009/0287195 A1 | 11/2009 | Altshuler et al. |
| 2009/0325885 A1 | 12/2009 | Miyata et al. |
| 2010/0152296 A1 | 6/2010 | Marmarinos et al. |
| 2010/0227799 A1 | 9/2010 | Trudel |
| 2010/0255045 A1 | 10/2010 | Eymard Du Vernet |
| 2010/0266989 A1 | 10/2010 | Piergallini et al. |
| 2011/0027753 A1 | 2/2011 | Maurat et al. |
| 2011/0081530 A1 | 4/2011 | Robinson et al. |
| 2011/0086060 A1 | 4/2011 | Bidamant et al. |
| 2011/0130459 A1 | 6/2011 | Spencer |
| 2011/0171310 A1 | 7/2011 | Gousse et al. |
| 2011/0182834 A1 | 7/2011 | Do et al. |
| 2011/0218482 A1 | 9/2011 | Piergallini et al. |
| 2011/0224599 A1 | 9/2011 | Piergallini et al. |
| 2012/0045516 A1 | 2/2012 | Kim |
| 2012/0095455 A1 | 4/2012 | Rodmond et al. |
| 2012/0171641 A1 | 7/2012 | Piergallini et al. |
| 2012/0317731 A1 | 12/2012 | Jiang et al. |

(56) References Cited

U.S. PATENT DOCUMENTS

| | | |
|---|---|---|
| 2013/0122467 A1 | 5/2013 | Piergallini et al. |
| 2013/0281913 A1 | 10/2013 | Piergallini et al. |
| 2014/0105832 A1 | 4/2014 | Loupis et al. |
| 2014/0276354 A1 | 9/2014 | Piergallini et al. |
| 2014/0303547 A1 | 10/2014 | Loupis et al. |
| 2015/0065453 A1 | 3/2015 | Piergallini et al. |
| 2015/0119788 A1 | 4/2015 | Loupis et al. |
| 2015/0290103 A1 | 10/2015 | Piergallini et al. |
| 2015/0290320 A1 | 10/2015 | Piergallini et al. |
| 2015/0306131 A1 | 10/2015 | Piergallini et al. |

FOREIGN PATENT DOCUMENTS

| | | |
|---|---|---|
| CA | 2457590 A1 | 3/2003 |
| CA | 2551613 | 12/2005 |
| CA | 2580381 A1 | 1/2006 |
| CA | 2632187 A1 | 7/2007 |
| CA | 2677468 A1 | 8/2008 |
| CA | 2797867 A1 | 11/2011 |
| CA | 2809405 A1 | 1/2012 |
| CN | 101304766 A | 11/2008 |
| CN | 101594904 A | 12/2009 |
| CN | 102133208 A | 7/2011 |
| DE | 2935450 A1 | 3/1981 |
| EP | 0356868 A2 | 3/1990 |
| EP | 0380157 A1 | 8/1990 |
| EP | 0704539 A2 | 4/1996 |
| EP | 0717983 A1 | 6/1996 |
| EP | 1235543 A1 | 9/2002 |
| EP | 1235544 A1 | 9/2002 |
| EP | 1778294 | 4/2005 |
| EP | 1749532 A1 | 2/2007 |
| EP | 1779891 A1 | 5/2007 |
| EP | 1951184 | 8/2008 |
| EP | 2338465 | 6/2011 |
| JP | 02-233612 | 9/1990 |
| JP | 03-169805 | 7/1991 |
| JP | 04-219756 | 8/1992 |
| JP | H10182390 | 7/1998 |
| JP | H10330235 | 12/1998 |
| JP | H092925 | 1/1999 |
| JP | 2000-053550 | 2/2000 |
| JP | 2001-511137 | 8/2001 |
| JP | 2001-279838 A | 10/2001 |
| JP | 2002-502864 | 1/2002 |
| JP | 2002-226349 | 8/2002 |
| JP | 2002-293747 A | 10/2002 |
| JP | 2003-503527 A | 1/2003 |
| JP | 2003-339875 | 2/2003 |
| JP | 2003-506488 A | 2/2003 |
| JP | 2008-210829 A | 4/2008 |
| JP | 2008-510829 A | 4/2008 |
| JP | 2008-231010 A | 10/2008 |
| JP | 2009-013132 A | 1/2009 |
| JP | 2009-514943 A | 4/2009 |
| JP | 2009-149692 A | 7/2009 |
| JP | 2012-508189 A | 4/2012 |
| JP | 2012-508190 A | 4/2012 |
| JP | 2013-525380 | 6/2013 |
| KR | 1020070017292 | 2/2007 |
| KR | 2008-0108618 A | 12/2008 |
| KR | 2011-0090983 A | 8/2011 |
| SG | 184945 A1 | 11/2012 |
| WO | WO 1981000513 A1 | 3/1981 |
| WO | WO 1990009779 | 9/1990 |
| WO | WO 1991662530 A1 | 3/1991 |
| WO | WO 1997021420 A1 | 6/1997 |
| WO | WO 1998011827 A1 | 3/1998 |
| WO | WO 1998610738 A1 | 3/1998 |
| WO | WO 1998023219 A1 | 6/1998 |
| WO | WO 1998030169 A1 | 7/1998 |
| WO | WO 1998033761 A1 | 8/1998 |
| WO | WO 1998036700 A1 | 8/1998 |
| WO | WO 1999039238 A1 | 8/1999 |
| WO | WO 1999040870 A1 | 8/1999 |
| WO | WO 1999049823 | 10/1999 |
| WO | WO 1999063900 A1 | 12/1999 |
| WO | WO 2000040266 | 7/2000 |
| WO | WO 2001000190 | 1/2001 |
| WO | WO 2001012181 | 2/2001 |
| WO | WO 2001035906 A2 | 5/2001 |
| WO | WO 2002022097 | 3/2002 |
| WO | WO 2002087642 | 11/2002 |
| WO | WO 2003000215 | 1/2003 |
| WO | WO 2003017824 | 3/2003 |
| WO | WO 2003061696 A2 | 7/2003 |
| WO | WO 2003086215 | 10/2003 |
| WO | WO 2003099247 A1 | 12/2003 |
| WO | WO 2004028498 | 4/2004 |
| WO | WO 2004073540 A2 | 9/2004 |
| WO | WO 2004081222 A2 | 9/2004 |
| WO | WO 2005009604 A1 | 2/2005 |
| WO | WO 2005051305 A2 | 6/2005 |
| WO | WO 2006014597 A1 | 2/2006 |
| WO | 2006/027664 A2 | 3/2006 |
| WO | WO 2006032847 A1 | 3/2006 |
| WO | WO 2006047868 A1 | 5/2006 |
| WO | WO 2006072243 A1 | 7/2006 |
| WO | WO 2006125650 A1 | 11/2006 |
| WO | 2006/135344 A1 | 12/2006 |
| WO | WO 2006135344 A1 | 12/2006 |
| WO | WO 2007087259 | 2/2007 |
| WO | WO 2007025244 A2 | 3/2007 |
| WO | WO 2007080453 A2 | 7/2007 |
| WO | WO 2007127172 | 11/2007 |
| WO | WO 2008011707 A1 | 1/2008 |
| WO | WO 2008013962 A2 | 1/2008 |
| WO | WO 2008052081 A2 | 5/2008 |
| WO | WO 2008096182 A1 | 8/2008 |
| WO | 2008/139601 A1 | 11/2008 |
| WO | WO 2009089345 A2 | 7/2009 |
| WO | WO 2009089346 A2 | 7/2009 |
| WO | WO 2010051636 A1 | 5/2010 |
| WO | WO 2010051641 A1 | 5/2010 |
| WO | WO 2010070292 A1 | 6/2010 |
| WO | WO 2011006263 A1 | 1/2011 |
| WO | WO 2011058448 A2 | 5/2011 |
| WO | WO 2011134087 A1 | 11/2011 |
| WO | WO 2012011875 A1 | 1/2012 |
| WO | WO 2012072980 | 6/2012 |
| WO | WO 2012126120 A1 | 9/2012 |
| WO | WO 2013155620 A1 | 10/2013 |
| WO | WO 2014040176 A1 | 3/2014 |
| WO | WO 2014040177 | 3/2014 |
| WO | WO 2014042936 | 3/2014 |
| WO | 2016/065488 A1 | 5/2016 |
| WO | 2017/201615 A1 | 11/2017 |

OTHER PUBLICATIONS

English abstract for KR 2008-0108618 provided.
English abstract for KR 2011-0090983 provided.
The Office Action issued from the Brazilian Patent Office dated Sep. 19, 2019.
Mintel, "Effervescent Tablets", Database GNPD [Online], May 2009, XP002769876, Database accession No. 1089966 Ingredients.
Brock et al., "Use of In Vitro and In Vivo Data in the Design, Development, and Quality Control of Sustained-Release Decongestant Dosage Forms", Pharmacotheapy, 1994, vol. 14, pp. 430-437.
Durrani et al., "Studies on Drug Release Kinetics from Carbopal® 934P Tablets", Pharmaceutical Res. Supp. 8:S135, 1991—abstract only.
Samson et al., "Wound-Healing Technologies: Low-Level Laser and Vacuum-Assisted Closure", Evidence Report/Technotogy Assessment 2004, 111, pp. 1-97 https://www.ncbi.nlm.nih.gov/books/NBK37464/toc/?report=reader.
Sutyagin et al., "Chemistry and Physics of Polymers: a text book Tomsk", TPU Publishers, 2003-208 p. English abstract provided.
Jarmolinska et al., "Matrix metalloproteinases and inhibitors: classification, mechanism of action", Journal of Obstetrics and Gynecological Diseases, vol. LXI 113-125, 2012 [title translated from Russian].

(56) References Cited

OTHER PUBLICATIONS

Alster et al., "Photodynamic therapy: practical cosmetic applications", Journal of Drugs in Dermatology, 5(8):764-768 (2006).
Antunes et al., "Evaluation of the clastogenicity and anticlastogenicity of the carotenoid bixin in the human lymphocyte cultures", Mutation Reasearch, 585(1-2):113-9 (2005).
Ariizumi et al., "Clinical evaluation of a topical applicant TSG-88 for periodontal disease", Dental Drug Therapy, 10(2):157-168 (1991).
Berneburg et al., "Phototherapy with narrowband UVB", Acta Dermato-Venereologica, 85:1-11 (2005).
Chen et al., "Study of the chemiluminescent characteristics of some xanthone dyes", Analytica Chimica Acta, 292(1-2): 159-167 (1994).
Colman et al., "The healing of wounds in the skin of piglets treated with benzoyl peroxide", The Journal of Dermatologic Surgery and Oncology, 4(9):705-707 (1978).
Darzynkiewicz et al., Photosensitizing effects of the tricyclic heteroaromatic cationic dyes Pyronin Y and Toluidine Blue O (tolonium chloride), Cancer Research, 48(5): 1295-1299 (1998).
De et al., "Environmental effects on the aggregation of some xanthene dyes used in lasers", Spectrochimica Acta Part A: Molecular and Biomolecular Spectroscopy, 61(8):1821-1833 (2005).
Decraene et al., "Cellulose acetate containing Toluidine Blue and Rose Bengal is an effective antimicrobial coating when exposed to white light", Applied and Env. Microbiology, 72:6 (4436-4439) (Jun. 2006).
Eurasian Search Report, Serial No. 201291068, dated May 29, 2013 with English translation (3 pages).
European Search Report and Written Opinion, Application No. 11161795, dated May 23, 2011 (6 pages).
European Supplementary Search Report, Application No. EP09824320, dated Mar. 28, 2012 (12 pages).
FDA, Color Additive Status List, http://www.cfsanJda.gov/-dms/opa-appc.html, downloaded Jun. 18, 2008 (13 pages).
FDA, Product Glassification Database Search, http://www.accessdata.fda.gov/scripts/cdrh/cfdocs/cped/classification/c.f?ID-3964, Device: Eosin y: database, downloaded Jun. 18, 2008 (2 pages).
Fisher Scientific, "Material Safety Data Sheet: Sodium acetate buffer", https://fscimagef.fishersci.com/msds/91502.htm (ACC #91502) (Apr. 13, 2000) (5 pages).
Goldberg, "Photodynamic therapy in skin rejuvenation", Clinics in Dermatology, 26(6):608-613 (2008).
Jankowski et al., "The action of photosensitizers and serum in a bactericidal process. II. The effects of dyes: Hypericin, Eosin Y and Saphranine O", Polish Journal of Microbiology, 54(4): 323-230 (2005).
Kelly et a., "Combined photodynamic and photothermal induced injury enhances damage to in vivo model blood vessels", Lasers in Surgery and Medicine, 34(5): 407-413 (2004).
McCullach et al., "Photosensitized destruction of Chlorella vulgaris by Methylene Blue or Nuclear Fast Red combined with hydrogen peroxide under visible light irradiation", Environmental Science and Technology, 40(7):2421-2425 (2006).
Meisel et al., "Photodynamic therapy for periodontal diseases: state of the art", Journal of Photochemistry and Photobiology B: Biology, 79:159-170 (2005).
Mintel, "Gold Bear Gums", http://gnpd.com, Aug. 2, 2008 (3 pages).
Mintel, "Teens Braces Cleaner", http://gnpd.com, Jan. 2004 (2 pages).
Montenegro et al., "Model Studies on the photosensitized isomerization of bixin", Journal of Agriculture and Food Chemistry, 52(2): 367-73 (2004).
Nolan et al., "The efficacy of topical hyaluronic acid in the management of oral lichen planus", Journal of Oral Pathology and Medicine, 38(3): 299-303 (2006).
Olympus America Inc., "Special characteristics of common biological stains", http://micro.magnet.fsu.edu/primer/photomicrography/bwstainchart.html, Apr. 30, 2000 (3 pages).

PCT International Preliminary Report on Patentability and Written opinion for International Serial No. PCT/CA2013/000787, dated Nov. 27, 2013 (9 pages).
PCT International Search Report and Written Opinion for International Application No. PCT/CA2014/000161, dated May 30, 2014 (12 pages).
PCT International Search Report and Written Opinion for International Application No. PCT/GR2007/000006, dated Oct. 12, 2007 (8 pages).
PCT International Search Report and Written Opinion for International Application No. PCT/IB2006/004034, dated Sep. 20, 2007 (13 pages).
PCT International Search Report and Written Opinion for International Serial No. PCT/CA2011/050261, dated Aug. 4, 2011 (6 pages).
PCT International Search Report and Written Opinion for International Serial No. PCT/CA2012/050177, dated Jun. 28, 2012 (8 pages).
PCT International Search Report Corrected for International Application No. PCT/CA2014/000261, dated Jul. 23, 2014 (7 pages).
PCT International Search Report for International Application No. PCT/CA2009/001615, dated Feb. 9, 2010 (9 pages).
PCT International Search Report for International Application No. PCT/CA2013/000395 dated Jul. 15, 2013 (12 pages).
PCT International Search Report for International Application No. PCT/CA2013/000786, dated Jan. 8, 2014 (16
Publication date of following document established by Internet Archive Wayback Machine (3 pages) <URL: <http://web.archive.org/web/20090208211504/http://en.wikipedia.org/wiki/Eosin Aug. 2, 2009.
Resources: Fluorochrome absorption emission wavelenghts [Online] XP002449595 Retrieved from the Internet: URL: http://www.sciencegateway.org/resources/fae1.htm> [retrieved on Sep. 6, 2007] see p. 2: Rhodamine WT emission nm 555 p. 2 (12 pages).
Rodgers, Fluorescence Polarization Standards for High-Throughput Screening and Imaging, 2002, BioTechniques 32:34-42.
Roy et al., "Dermal wound healing is subject to redox control", Molecular Therapy, 13(1): 211-220 (2006).
Sezer et al., "Topical drug delivery using chitosan nano- and microparticles", Expert Opinion in Drug Delivery, inform UK, 9(9):1129-1146 (2012).
Slyusareva et al., "Spectral and Photophysical Properties of Flurone Dyes in Bio-Related Films and Methanol", Journal of Photochemistry and Photobiology A; Chemistry 208 (2009), pp. 131-140.
Steinberg et al., "Genetic and physiological effects of noncoherent visible light combined with hydrogen peroxide on Streptococcus mutans in biofilm", Antimicrobial Agents and Chemotherapy, 52(7):2626-2631 (2008).
Subba et al., "Photocatalytic transformation of dyes and by-products in the presence of hydrogen peroxide", Environmental Technology, 24(8): 1025-1030 (2003).
Sun, "Lasers and Light Amplification in Dentistry", retrieved online at http://www.sundds.comllaser/, downloaded Jun. 23, 2005 (14 pages).
Tao et al., "Gastrointestinal Patch Systems for Oral Drug Delivery", Drug Discovery Today, vol. 10, No. 13, Jul. 2005, pp. 909-915.
Thompson et al., "Fluorescence polarization standards for high-throughput screening and imaging", Bio Techniques, 32:34-42 (2002).
Tsuboi et al., "Photoluminescence Properties of Fluorone Dyes in Bio-related Films at Low Temperatures", Journal of Photochemistry and Photobiology A: Chemistry 222 (2011) pp. 336-342.
Gonzales et al., "Photodynamic inactivation of microorganisms as an innovative approach to kill mucocutaneous and skin mircroorganisms", Giornale Italiano Di Dermatologia e Venereologia, 145, pp. 477-489 (2010).
Hu, "Adaptive and Functional Polymers, Textiles and Their applications", Imperial College Press, (pp. 319-320 and pp. 325-326) (2011).
Mintel, "Active Plus Deep Cleaning Tablets", Database GNPD [Online], May 2007, XP002769877, Database accession No. 707777 Ingredients.

(56) References Cited

OTHER PUBLICATIONS

Elsaie et al., "Photodynamic therapy in the management of acne: an update", J. Cosm. Derm., 9, pp. 211-217, 2010 (abstract only).

BIOPHOTONIC COMPOSITIONS AND METHODS FOR PROVIDING BIOPHOTONIC TREATMENT

CROSS-REFERENCE TO RELATED APPLICATIONS

This application is a continuation application of U.S. patent application Ser. No. 15/201,111, filed on Jul. 1, 2016, which is a continuation application of U.S. patent application Ser. No. 13/830,488, filed Mar. 14, 2013, which claims the benefit of U.S. Provisional Application Nos. 61/636,480, filed Apr. 20, 2012; 61/701,502, filed Sep. 14, 2012; 61/636,574, filed on Apr. 20, 2012; 61/701,510, filed on Sep. 14, 2012; 61/636,577, filed on Apr. 20, 2012; 61/701,513, filed on Sep. 14, 2012; and 61/766,611, filed on Feb. 19, 2013; the disclosures of which are hereby incorporated by reference in their entireties.

BACKGROUND OF THE DISCLOSURE

Phototherapy has recently been recognized as having wide range of applications in both the medical, cosmetic and dental fields for use in surgeries, therapies and examinations. For example, phototherapy has been developed to treat cancers and tumors with lessened invasiveness. Phototherapy has also been used to disinfect target sites as an antimicrobial treatment. Phototherapy has also been found to promote wound healing.

Photodynamic therapy is a type of phototherapy which involves a step of systemic administration or uptake of a photosensitive agent into the diseased or injured tissue, which step is followed by site-specific application of activating light (photodynamic therapy). Such regimens, however, are often associated with undesired side-effects, including systemic or localized toxicity due to the direct contact of the photosensitive agents with the tissues. Moreover, such existing regimens often demonstrate low therapeutic efficacy due to, for example, the poor uptake of the photosensitive agents into the target tissues. Therefore, it is an object of the present disclosure to provide new and improved compositions and methods useful in phototherapy.

SUMMARY OF THE DISCLOSURE

The present disclosure provides topical biophotonic compositions and methods useful in phototherapy. In particular, the biophotonic compositions of the present disclosure may contain a gelling agent that provides a barrier such that the chromophore(s) or photosensitive agent(s) and other components of the topical biophotonic compositions are not in substantial contact with the target tissues, and/or do not penetrate the target tissues. Put another way, the biophotonic compositions of the present disclosure may contain a gelling agent, which provides a barrier rendering the compositions substantially resistant to leaching. The use of such biophotonic topical compositions in phototherapy would therefore not involve substantial direct contact of the target tissues with a photosensitizing agent or chromophore, which may be potentially toxic to or may cause undesired side effects at the tissues.

In some aspects, there is provided a topical biophotonic composition comprising at least a first chromophore and a gelling agent, wherein the biophotonic composition is substantially resistant to leaching such that less than 15% of the total chromophore amount leaches out of the biophotonic composition into tissue. In some embodiments, the biophotonic composition is substantially resistant to leaching such that less than 15% of total chromophore amount leaches out of the biophotonic composition into tissue when in contact with the tissue for at least about, 5 minutes, about 10 minutes, about 15 minutes, about 20 minutes, about 25 minutes or about 30 minutes. In some embodiments, less than 15% of total chromophore amount leaches out of the biophotonic composition during a treatment time. The treatment time can be up to about 5 minutes, about 10 minutes, about 15 minutes, about 20 minutes, about 25 minutes, about 30 minutes.

In some aspects, there is provided a topical biophotonic composition comprising at least a first chromophore and a gelling agent, wherein the first chromophore is photoactive in the composition, and wherein the composition is substantially resistant to leaching such that less than 15% of total chromophore amount can leach out into tissue during a treatment time in which the composition is topically applied onto tissue. The treatment time may comprise the total length of time that the composition is in contact with tissues, or if different, the time of light illumination of the composition.

In some aspects, there is provided a topical biophotonic composition comprising at least a first chromophore and a gelling agent, wherein the biophotonic composition is a gel or a semi-solid and is substantially resistant to leaching such that less than 15% of the total chromophore amount leaches out of the biophotonic composition into tissue when in contact with tissue for at least about 5 minutes.

In some aspects, there is provided a topical biophotonic composition comprising at least a first chromophore and a gelling agent, wherein the biophotonic composition is substantially translucent and is substantially resistant to leaching such that less than 15% of the total chromophore amount leaches out of the biophotonic composition into tissue when in contact with tissue for at least about 5 minutes. By substantially translucent is meant having a transmission of more than about 20%.

In another aspect, there is provided a biophotonic composition comprising a first chromophore, wherein the composition is encapsulated in a membrane which limits leaching of the first chromophore such that less than 15% of the total chromophore amount leaches out into tissue when in contact with the tissue for at least about 5 minutes. The biophotonic composition may also comprise a carrier medium which may be a liquid, a gel or a semi-solid.

In certain embodiments of any of the foregoing or following, the biophotonic topical composition allows less than 30%, 25%, 20%, 15%, 10%, 5%, 1%, 0.8%, 0.5% or 0.1%, or essentially none of said chromophore content to leach out of the biophotonic composition.

In certain embodiments of any of the foregoing or following, the biophotonic topical composition further comprises a second chromophore. In certain embodiments of any of the foregoing or following, the first chromophore of the biophotonic topical composition has an emission spectrum that overlaps at least 5%, 10%, 20%, 25%, 30%, 40%, 50%, 60%, 70% with an absorption spectrum of the second chromophore, when present. In some embodiments, the first chromophore of the biophotonic topical composition has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore when present.

In certain embodiments of any of the foregoing or following, the gelling agent comprises a hygroscopic substance. In addition or in the alternative, the gelling agent may also be a hydrophilic polymer, a hydrated polymer or a lipid. In certain embodiments, the gelling agent comprises one or more of glycerin, glycols such as propylene glycol, polyacrylic acid polymers, hyaluronic acid, glucosamine sulphate or gelatin.

In certain embodiments of any of the foregoing or following, the gelling agent is a high molecular weight, cross-linked polyacrylic acid polymer having a viscosity in the range of about 20,000-80,000, 20,000-100,000, 25,000-90,000, 30,000-80,000, 30,000-70,000, 30,000-60,000, 25,000-40,000 cP. In certain embodiments, the cross-linked polyacrylic acid polymer is a carbomer selected from the group consisting of, but not limited to, Carbopol® 71G NF, 971P NF, 974P NF, 980 NF, 981 NF, 5984 EP, ETD 2020NF, Ultrez 10 NF, 934 NF, 934P NF, 940 NF, 941 NF, or 1342 NF.

In certain embodiments of any of the foregoing or following, the biophotonic composition is substantially translucent and/or transparent. In certain embodiment, the biophotonic composition has a translucency of at least 70% at 460 nm. In other embodiments, the composition has a translucency of at least 20%, 30%, 40%, 50%, 60%, 70%, 75%, 85%, 90%, 95% or 100% at 460 nm.

In certain embodiments of any of the foregoing or following, the biophotonic composition is a gel or a semi-solid.

In certain embodiments of any of the foregoing or following, the biophotonic composition is encapsulated in a transparent, impermeable membrane, or a breathable membrane which allows permeation of gases but not liquids. The membrane may comprise a lipid.

In certain embodiments of any of the foregoing or following, the biophotonic composition further comprises an oxygen-generating agent. In some embodiments, the oxygen-generating agent comprises hydrogen peroxide, carbamide peroxide, benzoyl peroxide, or water.

In certain embodiments of any of the foregoing or following, at least one of the chromophores, for example, the first chromophore, photobleaches during illumination with light. In certain embodiments, at least one of the chromophores, for example, the first chromophore emits fluorescence upon illumination with light.

In certain embodiments of any of the foregoing or following, illumination of the biophotonic topical composition with light causes a transfer of energy from the first chromophore to the second chromophore. In some embodiments, the second chromophore emits fluorescence and/or generates reactive oxygen species after absorbing energy from the first chromophore.

In certain embodiments of any of the foregoing or following, the biophotonic composition does not generate a substantial amount of heat following illumination with light. In some embodiments, the energy emitted by the biophotonic composition does not cause tissue damage.

In certain embodiments of any of the foregoing or following, the first chromophore of the biophotonic topical composition absorbs light at a wavelength of 200-600 nm, or 400-800 nm.

In certain embodiments of any of the foregoing or following, the first chromophore absorbs light at a wavelength in the range of the visible spectrum.

In certain embodiments of any of the foregoing or following, the biophotonic composition comprises a second chromophore, which absorbs light at a wavelength in the range of the visible spectrum. In some embodiments, the second chromophore has an absorption wavelength that is relatively longer than that of the first chromophore, for example, 10-100 nm, 20-80 nm, 25-70 nm, or 30-60 nm longer.

In certain embodiments of any of the foregoing or following, the first chromophore of the biophotonic topical composition is present in an amount of 0.01-40% per weight of the composition, and the second chromophore, when present, is present in an amount of 0.001-40% per weight of the composition. In certain embodiments, the total weight per weight of chromophore or combination of chromophores may be in the amount of about 0.001-40.05% per weight of the composition.

In certain embodiments of any of the foregoing or following, the biophotonic composition may be applied to or impregnated into a material such as a pad, a dressing, a woven or non-woven fabric or the like. The impregnated material may be used as a mask (e.g. a face mask) or a dressing.

In certain embodiments of any of the foregoing or following, the biophotonic composition further comprises at least one waveguide within or adjacent to the composition. The waveguide can be a particle, a fibre or a fibrillar network made of a material which can transmit and/or emit light.

In certain embodiments of any of the foregoing or following, the composition does not comprise silica.

In certain embodiments of any of the foregoing or following, the first or second chromophore is a fluorescent chromophore ('fluorophore').

In certain embodiments of any of the foregoing or following, the first or second chromophore is a fluorescent xanthene. In some embodiments, the first or second chromophore is selected from Eosin Y, Erythrosin B, Fluorescein, Rose Bengal and Phloxin B. In certain embodiments, the biophotonic composition comprises at least two of Eosin Y, Erythrosin B, Fluorescein, Rose Bengal and Phloxin B.

In certain embodiments of any of the foregoing or following, the first chromophore is Eosin Y. In other embodiments, the first chromophore is Fluorescein. In other embodiments, the first chromophore is Rose Bengal. In some embodiments, the biophotonic composition comprises Eosin and Fluorescein. In other embodiments, the biophotonic composition comprises Eosin and Rose Bengal. In other embodiments, the biophotonic composition comprises Fluorescein and Rose Bengal. In other embodiments, the biophotonic composition comprises Fluorescein and Rose Bengal.

In another aspect, there is provided a method for providing biophotonic therapy to a wound, comprising: applying a biophotonic composition to a wound, wherein the biophotonic composition comprises at least at least a first chromophore and a gelling agent; and illuminating the biophotonic composition with light having a wavelength that overlaps with an absorption spectrum of the first chromophore; wherein the gelling agent renders the biophotonic composition substantially resistant to leaching such that less than 15% of the total chromophore amount leaches out of the composition into tissue. In certain embodiments, the composition is substantially resistant to leaching such that less than 15% of the total chromophore amount leaches out of the biophotonic composition into tissue during a treatment time in which the composition is topically applied onto tissue. In some embodiments, the biophotonic is substantially resistant to leaching such that less than about 15% of total chromophore content leaches out of the biophotonic composition during a treatment time of at least 5 minutes, at least 10 minutes, at least 15 minutes, at least 20 minutes, at least 25 minutes or at least 30 minutes.

In some embodiments of the method for providing biophotonic therapy to a wound, the method promotes wound healing. In certain embodiments of the method, the wound as described herein includes for example chronic or acute wounds, such as diabetic foot ulcers, pressure ulcers, venous ulcers or amputations. In some embodiments of the method for providing biophotonic therapy to a wound, the method promotes reduction of scar tissue formation.

In yet another aspect, there is provided a method for biophotonic treatment of acne comprising: applying a biophotonic composition to a target skin tissue, wherein the biophotonic composition comprises at least a first chromophore and a gelling agent; and illuminating said biophotonic composition with light having a wavelength that overlaps with an absorption spectrum of the first chromophore; wherein the gelling agent renders the biophotonic composition substantially resistant to leaching such that less than 15% of the total chromophore amount leaches out of the composition into tissue. In certain embodiments, the composition is substantially resistant to leaching such that less than 15% of the total chromophore amount leaches out of the biophotonic composition into tissue during a treatment time in which the composition is topically applied onto tissue. In some embodiments, the biophotonic is substantially resistant to leaching such that less than about 15% of total chromophore content leaches out of the biophotonic composition during a treatment time of at least 5 minutes, at least 10 minutes, at least 15 minutes, at least 20 minutes, at least 25 minutes or at least 30 minutes.

In certain embodiments of the method for biophotonic treatment acne, the treatment can be applied to the skin tissue, such as on the face, once, twice, three times, four times, five times or six times a week, daily, or at any other frequency. The total treatment time can be one week, two weeks, three weeks, four weeks, five weeks, six weeks, seven weeks, eight weeks, nine weeks, ten weeks, eleven weeks, twelve weeks, or any other length of time deemed appropriate. In certain embodiments, the face may be split into separate areas (cheeks, forehead), and each area treated separately. For example, the composition may be applied topically to a first portion, and that portion illuminated with light, and the biophotonic composition then removed. Then the composition is applied to a second portion, illuminated and removed. Finally, the composition is applied to a third portion, illuminated and removed.

In certain embodiments of the method for biophotonic treatment of wounds, the treatment can be applied in or on the wound once, twice, three times, four times, five times or six times a week, daily, or at any other frequency. The total treatment time can be one week, two weeks, three weeks, four weeks, five weeks, six weeks, seven weeks, eight weeks, nine weeks, ten weeks, eleven weeks, twelve weeks, or any other length of time deemed appropriate.

The disclosed methods for treating acne or wounds may further include, for example, administering a systemic or topical drug before, during or after the biophotonic treatment. The drug may be an antibiotic, a hormone treatment, or any other pharmaceutical preparation which may help to treat acne or wounds. The combination of a systemic treatment together with a topical biophotonic treatment can reduce the duration of systemic treatment time.

In yet another aspect, there is provided a method for biophotonic treatment of a skin disorder comprising: applying a biophotonic composition to a target skin tissue, wherein the biophotonic composition comprises at least first chromophore and a gelling agent; and illuminating said biophotonic composition with light having a wavelength that overlaps with an absorption spectrum of the first chromophore; wherein the gelling agent renders the biophotonic composition substantially resistant to leaching such that less than 15% of the total chromophore amount leaches out of the composition into tissue. In certain embodiments, the composition is substantially resistant to leaching such that less than 15% of the total chromophore amount leaches out of the biophotonic composition into tissue during a treatment time in which the composition is topically applied onto tissue. In some embodiments, the biophotonic is substantially resistant to leaching such that less than about 15% of total chromophore content leaches out of the biophotonic composition during a treatment time of at least 5 minutes, at least 10 minutes, at least 15 minutes, at least 20 minutes, at least 25 minutes or at least 30 minutes.

In yet another aspect, the present disclosure provides a method for promoting skin rejuvenation, comprising: topically applying a biophotonic composition to a target skin tissue, wherein the biophotonic composition comprises at least a first chromophore and a gelling agent; and illuminating said biophotonic composition with light having a wavelength that overlaps with an absorption spectrum of the first chromophore; wherein the gelling agent renders the biophotonic composition substantially resistant to leaching such that less than 15% of the total chromophore amount leaches out of the composition into tissue. In certain embodiments, the composition is substantially resistant to leaching such that less than 15% of the total chromophore amount leaches out of the biophotonic composition into tissue during a treatment time in which the composition is topically applied onto tissue. In some embodiments, the biophotonic is substantially resistant to leaching such that less than about 15% of total chromophore content leaches out of the biophotonic composition during a treatment time of at least 5 minutes, at least 10 minutes, at least 15 minutes, at least 20 minutes, at least 25 minutes or at least 30 minutes.

In yet another aspect, the present disclosure provides a method for cosmetic skin treatment, comprising: topically applying a biophotonic composition to a target skin tissue, wherein the biophotonic composition comprises at least a first chromophore and gelling agent; and illuminating said biophotonic composition with light having a wavelength that overlaps with an absorption spectrum of the first chromophore; wherein the gelling agent renders the biophotonic composition substantially resistant to leaching such that less than 15% of the total chromophore amount leaches out of the composition into tissue. In certain embodiments, the composition is substantially resistant to leaching such that less than 15% of the total chromophore amount leaches out of the biophotonic composition into tissue during a treatment time in which the composition is topically applied onto tissue. In some embodiments, the biophotonic is substantially resistant to leaching such that less than about 15% of total chromophore content leaches out of the biophotonic composition during a treatment time of at least 5 minutes, at least 10 minutes, at least 15 minutes, at least 20 minutes, at least 25 minutes or at least 30 minutes.

In yet another aspect, the present disclosure provides a method for treatment of periodontal disease, comprising: topically applying a biophotonic composition to a periodontal pocket, wherein the biophotonic composition comprises at least a first chromophore and a gelling agent; and illuminating said biophotonic composition with light having a wavelength that overlaps with an absorption spectrum of the first chromophore; wherein the gelling agent renders the biophotonic composition substantially resistant to leaching such that less than 15% of the total chromophore amount leaches out of the composition into periodontal tissue. In certain embodiments, the composition is substantially resistant to leaching such that less than 15% of the total chromophore amount leaches out of the biophotonic composition into periodontal tissue during a treatment time in which the composition is topically applied onto periodontal tissue. In some embodiments, the biophotonic is substantially resistant to leaching such that less than about 15% of total chromophore content leaches out of the biophotonic composition during a treatment time of at least 5 minutes, at least 10 minutes, at least 15 minutes, at least 20 minutes, at least 25 minutes or at least 30 minutes.

In certain embodiments of any method of the present disclosure, the biophotonic composition is illuminated for any time period per treatment in which the biophotonic composition is activated, for example 1 to 30 minutes. The distance of the light source from the biophotonic composition can be any distance which can deliver an appropriate light power density to the biophotonic composition and/or the skin tissue, for example 5, 10, 15 or 20 cm. The biophotonic composition is applied topically at any suitable thickness. Typically, the biophotonic composition is applied topically to skin or wounds at a thickness of at least about 2 mm, about 2 mm to about 10 mm.

In certain embodiments, the method of the present disclosure comprises a step of illuminating the biophotonic composition for a period of at least 30 seconds, 2 minutes, 3 minutes, 5 minutes, 7 minutes, 10 minutes, 15 minutes, 20 minutes, 25 minutes, or 30 minutes. In some embodiments, the biophotonic composition is illuminated for a period of at least 3 minutes.

In certain embodiments of the methods of the present disclosure, the biophotonic composition is removed from the site of a treatment following application of light. Accordingly, the biophotonic composition is removed from the site of treatment within at least 30 seconds, 2 minutes, 3 minutes, 5 minutes, 7 minutes, 10 minutes, 15 minutes, 20 minutes, 25 minutes or 30 minutes after application. In some embodiments, the biophotonic composition is illuminated for a period of at least 3 minutes. In some embodiments, the biophotonic composition is removed after a period of at least 3 minutes post application of the biophotonic composition to treatment site.

In certain other embodiments, the biophotonic composition is kept in place for up to one, two or three weeks, and illuminated with light which may include ambient light at various intervals. In this case, the composition may be covered up in between exposure to light. For example, the biophotonic composition may be soaked in a dressing and placed inside or over a wound and be left in place for an extended period of time (e.g. more than one day).

DETAILED DESCRIPTION (1) Overview

Figure 1:
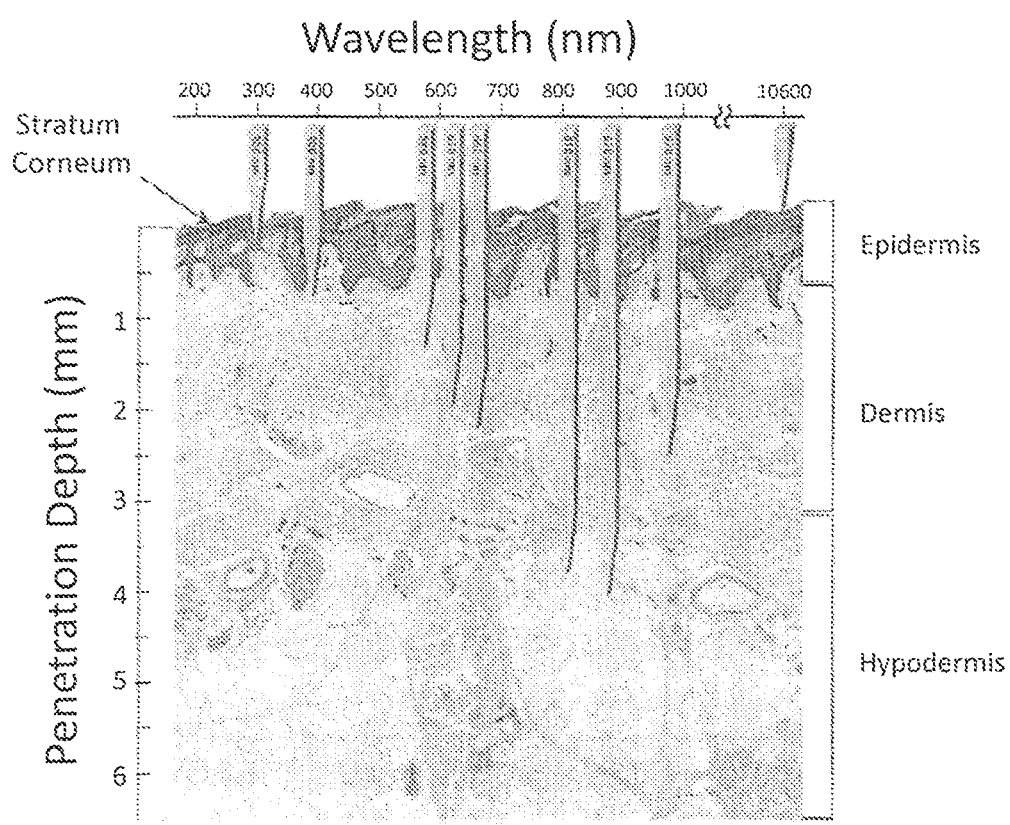
FIG. 1 depicts absorption of light in the various layers of the skin (Samson et al. *Evidence Report/Technology Assessment* 2004, 111, pages 1-97).

Phototherapy regimens have been developed to promote wound healing, rejuvenate facial skins and treat various skin disorders. However, these methods require direct application of a photosensitive agent (or chromophore) to the target skin and/or uptake of the photosensitive agent (or chromophore) into the skin cells. As mentioned above, the direct contact of the photosensitive agent with the tissue can lead to undesired side-effects, including cellular damage/destruction and systemic or localized toxicity to the patient. Moreover, many existing phototherapy regimens often demonstrate low therapeutic efficacy due to, for example, the poor update of the photosensitive agents into the skin cells the target site. For this reason, may regimens require a wait time of between about one and 72 hours to allow the internalization of the photosensitizer.

The present disclosure provides biophotonic compositions including a photoactive exogenous chromophore and methods useful for promoting wound healing, cosmetic treatment of skin such as skin rejuvenation, treating acne and treating other skin disorders, treating acute inflammation, which are distinguished from conventional photodynamic therapy. Biophotonic therapy using these compositions does not rely on internalization of the chromophore into cells or substantial contact with the cells or target tissues. Therefore, the undesired side effects caused by direct contact may be reduced, minimized, or prevented. At most, the chromophore has surface contact with the tissue to which the composition is applied.

(2) Definitions

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A. (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons. "Biophotonic composition" is a composition as described herein that may be activated by light to produce photons for biologically relevant applications.

"Topical composition" means a composition to be applied to body surfaces, such as the skin, mucous membranes, vagina, oral cavity, internal surgical wound sites, and the like. A topical composition may be in the form of, including, but not limited to, a cream, gel, ointment, lotion, levigate, solution, paste, putty, bioadhesive, salve, milk, impregnated material such as a pad, sheet, fabric or fibres, dressings, spray, suspension, foam, or the like.

Terms "chromophore", "photoactivating agent" and "photoactivator" are used herein interchangeably. A chromophore means a chemical compound, when contacted by light irradiation, is capable of absorbing the light. The chromophore readily undergoes photoexcitation and can then transfer its energy to other molecules or emit it as light.

"Photobleaching" means the photochemical destruction of a chromophore.

"Leaching" means the release of one or more components of a biophotonic composition (e.g., the chromophore(s)) from the composition to the surrounding environment such as for example the wound site or into the tissue being treated with the composition).

The term "actinic light" is intended to mean light energy emitted from a specific light source (e.g., lamp, LED, or laser) and capable of being absorbed by matter (e.g. the chromophore or photoactivator defined above). In a preferred embodiment, the actinic light is visible light.

As used herein, a "hygroscopic" substance is a substance capable of taking up water, for example, by absorption or adsorption even at relative humidity as low as 50%, at room temperature (e.g. about 25° C.).

"Impermeable membrane" means that the material contained within the membrane is sufficiently or substantially impermeable to the surrounding environment such that the migration of such material out of the membrane, and/or the migration of the environmental components (such as water) into the membrane, is so low as to having substantially no adverse impact on the function or activity of the materials retained within the membrane. The impermeable membrane may be 'breathable' in that gas flow through the membrane is permitted whilst the flow of liquid is not permitted. The impermeable membrane may also selectively allow the migration of some of the materials through the membrane but not others.

"Wound" means an injury to any tissue, including for example, acute, subacute, delayed or difficult to heal wounds, and chronic wounds. Examples of wounds may include both open and closed wounds. Wounds include, for example, burns, incisions, excisions, lesions, lacerations, abrasions, puncture or penetrating wounds, surgical wounds, contusions, hematomas, crushing injuries, ulcers (such as for example pressure, venous, pressure or diabetic), wounds caused by periodontitis (inflammation of the periodontium).

"Skin rejuvenation" means a process of reducing, diminishing, retarding or reversing one or more signs of skin aging. For instance, common signs of skin aging include, but are not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. According to the present disclosure, one or more of the above signs of aging may be reduced, diminished, retarded or even reversed by the compositions and methods of the present disclosure.

(3) Biophotonic Topical Compositions

The present disclosure provides biophotonic compositions. Biophotonic compositions are compositions that are, in a broad sense, activated by light (e.g., photons) of specific wavelength. These compositions contain at least one exogenous chromophore which is activated by light and accelerates the dispersion of light energy, which leads to light carrying on a therapeutic effect on its own, and/or to the photochemical activation of other agents contained in the composition (e.g., acceleration in the breakdown process of peroxide (an oxygen-releasing agent) when such compound is present in the composition or at the treatment site, leading to the formation of oxygen radicals, such as singlet oxygen).

In some aspects, the present disclosure provides biophotonic compositions comprising at least a first chromophore and a gelling agent, wherein the composition is substantially resistant to leaching such that a low chromophore amount leaches out of the biophotonic composition into tissue during treatment. In other aspects, the present disclosure provides a first composition and a second composition, wherein the first composition comprises an oxygen-releasing agent and the second composition comprises one or more chromophores, which, when mixed with the first composition and subsequently activated by light, disperses the light energy, leading to the photochemical activation of the oxygen-releasing agent contained in the mixture, which may lead to the formation of oxygen radicals, such as singlet oxygen.

Figure 2:
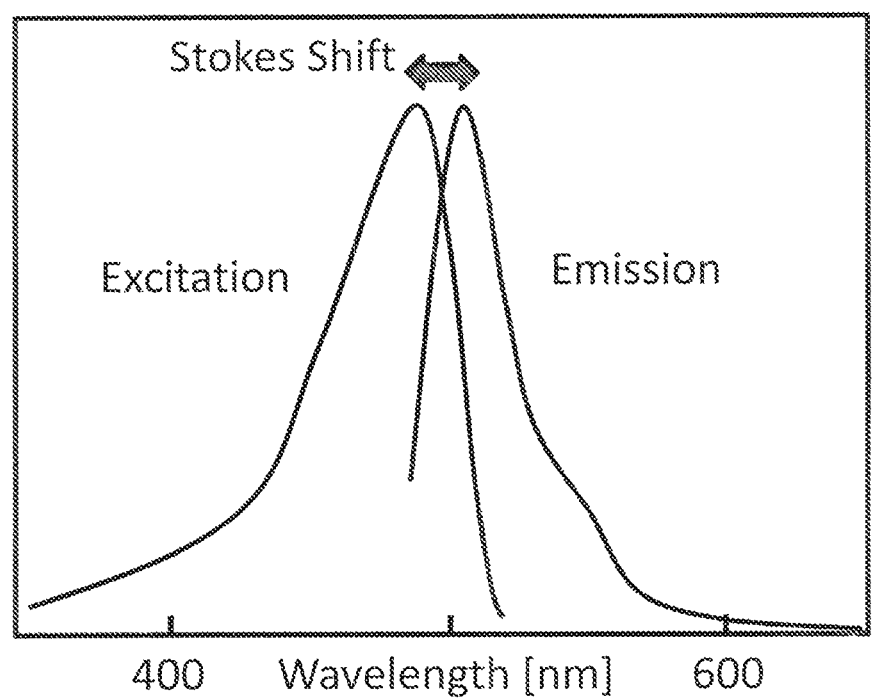
FIG. 2 illustrates the Stokes' shift.

When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths due to loss of energy in the conversion process. This is called the Stokes' shift and is illustrated in FIG. 2. In the proper environment (e.g., in a biophotonic composition) much of this energy is transferred to the other components of the composition or to the treatment site directly.

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light. Irradiating tissue with such a broad range of wavelengths, including in some embodiments the activating light which passes through the composition, may have different and complementary effects on the cells and tissues. Moreover, the generation of oxygen species by photoactivated chromophores has been observed by the inventors to cause micro-bubbling within the composition which can have a physical impact on the tissue to which it is applied, for example by dislodging biofilm and debridement of necrotic tissue or providing a pressure stimulation. The biofilm can also be pre-treated with an oxygen-releasing agent to weaken the biofilm before treating with the composition of the present disclosure.

The biophotonic compositions of the present disclosure are substantially transparent/translucent and/or have high light transmittance in order to permit light dissipation into and through the composition. In this way, the area of tissue under the composition can be treated both with the fluorescent light emitted by the composition and the light irradiating the composition to activate it. The % transmittance of the biophotonic composition can be measured in the range of wavelengths from 250 nm to 800 nm using, for example, a Perkin-Elmer Lambda 9500 series UV-visible spectrophotometer. In some embodiments, transmittance of the compositions disclosed herein is measured at 460 nm.

As transmittance is dependent upon thickness, the thickness of each sample can be measured with calipers prior to loading in the spectrophotometer. Transmittance values can be normalized to a thickness of 100 μm (or any thickness) according to:

$$F_{T-corr}(\lambda, t_2) = [e^{-\sigma_t(\lambda)t_1}]^{\frac{t_2}{t_1}} = [F_{T-corr}(\lambda, t_1)]^{\frac{t_2}{t_1}},$$

where $t_1$=actual specimen thickness, $t_2$=thickness to which transmittance measurements can be normalized.

In some embodiments, the biophotonic composition has a transparency or translucency that exceeds 15%, 20%, 30%, 40%, 50%, 55%, 60%, 65%, 70%, 75%, 80%, or 85% at 460 nm. In some embodiments, the transparency exceeds 70% at 460 nm, 86% at 460 nm, 87% at 460 nm, 880 at 460 nm. 89% at 460 nm, 90% at 460 nm, 91% at 460 nm, 92% at 460 nm, 93% at 460 nm. 94% at 460 nm, 95% at 460 nm, 96% at 460 nm. 97% at 460 nm, 98% at 460 nm or 99% at 460 nm.

The biophotonic compositions of the present disclosure are for topical uses. These compositions may be described based on the components making up the composition. Additionally or alternatively, the compositions of the present disclosure have functional and structural properties and these properties may also be used to define and describe the compositions. Individual components of the composition of the present disclosure are detailed as below.

(a) Chromophores

The biophotonic topical compositions of the present disclosure comprise one or more chromophores, which can be considered exogenous, e.g., are not naturally present in skin or tissue.

Suitable chromophores can be fluorescent dyes (or stains), although other dye groups or dyes (biological and histological dyes, food colorings, carotenoids, naturally occurring fluorescent and other dyes) can also be used. Suitable photoactivators can be those that are Generally Regarded As Safe (GRAS). Photoactivators which are not well tolerated by the skin or other tissues can be included in the biophotonic composition in an encapsulated form.

In certain embodiments, the biophotonic topical composition of the present disclosure comprises a first chromophore which undergoes partial or complete photobleaching upon application of light. By photobleaching is meant a photochemical destruction of the chromophore which can generally be visualized as a loss of color.

In some embodiments, the first chromophore absorbs at a wavelength in the range of the visible spectrum, such as at a wavelength of about 380-800 nm, 380-700, or 380-600 nm. In other embodiments, the first chromophore absorbs at a wavelength of about 200-800 nm, 200-700 nm, 200-600 nm or 200-500 nm. In one embodiment, the first chromophore absorbs at a wavelength of about 200-600 nm. In some embodiments, the first chromophore absorbs light at a wavelength of about 200-300 nm. 250-350 nm. 300-400 nm. 350-450 nm, 400-500 nm. 400-600 nm, 450-650 nm. 600-700 nm, 650-750 nm or 700-800 nm.

It will be appreciated to those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectrum) measured in a biophotonic composition of the present disclosure.

The biophotonic compositions disclosed herein may include at least one additional chromophore. Combining chromophores may increase photo-absorption by the combined dye molecules and enhance absorption and photobiomodulation selectivity. This creates multiple possibilities of generating new photosensitive, and/or selective chromophores mixtures.

Figure 3:
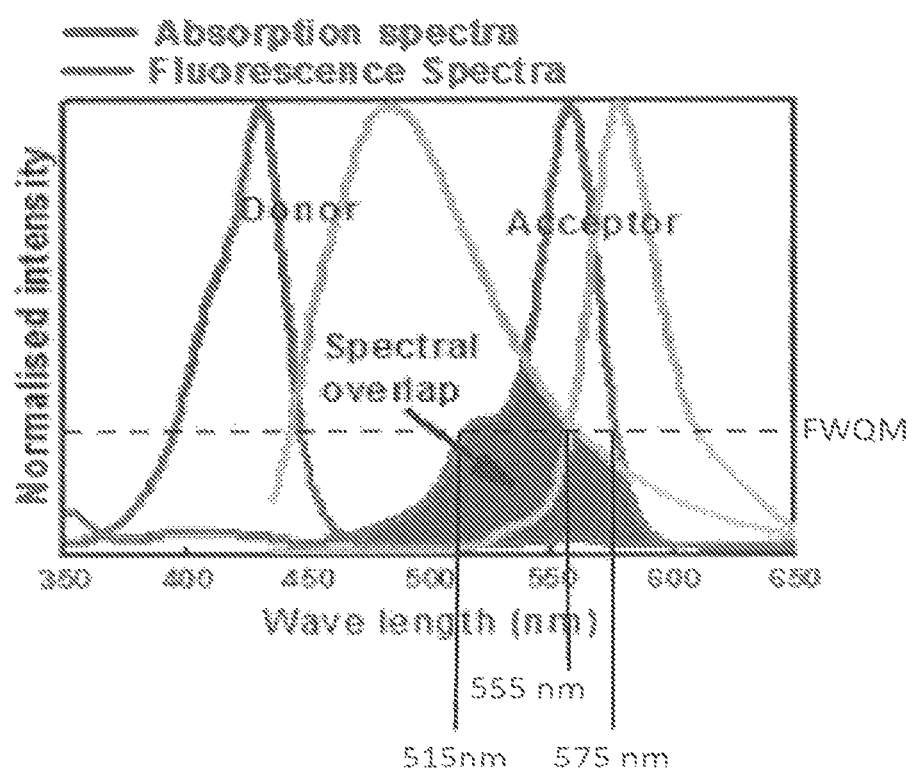
FIG. 3 illustrates the absorption and emission spectra of donor and acceptor chromophores. The spectral overlap between the absorption spectrum of the acceptor chromophore and the emission spectrum of the donor chromophore is also shown.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur the emission spectrum of the donor chromophore overlap with the absorption spectrum of the acceptor chromophore (FIG. 3).

Figure 4:
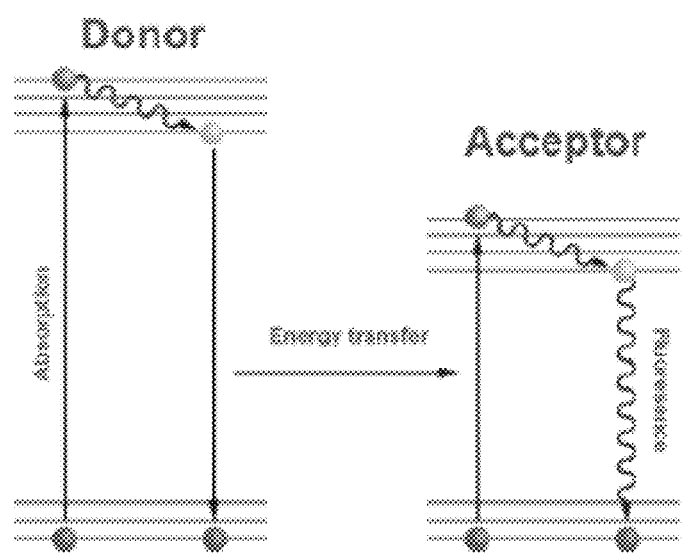
FIG. 4 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 4 is a Jablonski diagram that illustrates the coupled transitions involved between a donor emission and acceptor absorbance.

To enhance the energy transfer efficiency, the donor chromophore should have good abilities to absorb photons and emit photons. Furthermore, it is thought that the more overlap there is between the donor chromspheres' emission spectra and the acceptor chromophore's absorption spectra, the better a donor chromophore can transfer energy to the acceptor chromophore.

In certain embodiments, the biophotonic topical composition of the present disclosure further comprises a second chromophore. In some embodiments, the first chromophore has an emission spectrum that overlaps at least about 80%, 50%, 40%, 30%, 20%, 10% with an absorption spectrum of the second chromophore. In one embodiment, the first chromophore has an emission spectrum that overlaps at least about 20% with an absorption spectrum of the second chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore. % spectral overlap, as used herein, means the % overlap of a donor chromophore's emission wavelength range with an acceptor chromophore's absorption wavelength rage, measured at spectral full width quarter maximum (FWQM). For example, FIG. 3 shows the normalized absorption and emission spectra of donor and acceptor chromophores. The spectral FWQM of the acceptor chromophore's absorption spectrum is from about 60 nm (515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In certain embodiments, the second chromophore has an absorption wavelength that is relatively longer than that of the first chromophore within the range of about 50-250, 25-150 or 10-100 nm.

As discussed above, the application of light to the compositions of the present disclosure can result in a cascade of energy transfer between the chromophores. In certain embodiments, such a cascade of energy transfer provides photons that penetrate the epidermis, dermis and/or mucosa at the target tissue, including, such as, a site of wound, or a tissue afflicted with acne or a skin disorder. In some embodiments, such a cascade of energy transfer is not accompanied by concomitant generation of heat. In some other embodiments, the cascade of energy transfer does not result in tissue damage.

Optionally, when the biophotonic topical composition comprises a first and a second chromophore, the first chromophore is present in an amount of about 0.01-40% per weight of the composition, and the second chromophore is present in an amount of about 0.001-40% per weight of the composition. In certain embodiments, the total weight per weight of chromophore or combination of chromophores may be in the amount of about 0.01-40.001% per weight of the composition. In certain embodiments, the first chromophore is present in an amount of about 0.01-1%, 0.01-2%, 0.05-1%, 0.05-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-1%, 0.001-2%, 0.001-0.01%, 0.01-0.1%, 0.1-1.0%, 1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the total weight per weight of chromophore or combination of chromophores may be in the amount of about 0.01-1%, 0.01-2%, 0.05-2%, 0.5-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In some embodiments, the chromophore or chromophores are selected such that their emitted fluorescent light, on photoactivation, is within one or more of the green, yellow, orange, red and infrared portions of the electromagnetic spectrum, for example having a peak wavelength within the range of about 490 nm to about 800 nm. In certain embodiments, the emitted fluorescent light has a power density of between 0.005 to about 10 mW/cm$^2$, about 0.5 to about 5 mW/cm$^2$.

Suitable chromophores that may be used in the biophotonic topical compositions of the present disclosure include, but are not limited to the following:

Chlorophyll Dyes

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene Derivatives

Exemplary xanthene dyes include but are not limited to Eosin B (4',5'-dibromo,2',7'-dinitr-o-fluorescein, dianion); eosin Y; eosin Y (2',4',5',7'-tetrabromo-fluoresc-ein, dianion); eosin (2',4',5',7'-tetrabromo-fluorescein, dianion), eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachlor-o-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene Blue Dyes

Exemplary methylene blue derivatives include but are not limited to 1-methyl methylene blue; 1,9-dimethyl methylene blue; methylene blue; methylene blue (16 .mu.M); methylene blue (14 .mu.M); methylene violet; bromomethylene violet; 4-iodomethylene violet; 1,9-dimethyl-3-dimethyl-amino-7-diethyl-a-mino-phenothiazine; and 1,9-dimethyl-3-diethylamino-7-dibutyl-amino-phenot-hiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta. Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9. Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kemechtrot, Lac, Laccaic acid, Lauth's violet, Light green, Lissamine green SF, Luxol fast blue, Magenta 0, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins, Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In certain embodiments, the composition of the present disclosure includes any of the chromophores listed above, or a combination thereof, so as to provide a biophotonic impact at the application site. This is a distinct application of these agents and differs from the use of chromophores as simple stains or as a catalyst for photo-polymerization.

In some embodiments, the composition includes Eosin Y as a first chromophore and any one or more of Rose Bengal, Erythrosin, Phloxine B as a second chromophore. It is believed that these combinations have a synergistic effect as Eosin Y can transfer energy to Rose Bengal, Erythrosin or Phloxine B when activated. This transferred energy is then emitted as fluorescence or by production of reactive oxygen species. This absorbed and reemitted light is thought to be transmitted throughout the composition, and also to be transmitted into the site of treatment.

In further embodiments, the composition includes the following synergistic combinations: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal. Fluorescein and Erythrosine. Other synergistic chromophore combinations are also possible.

By means of synergistic effects of the chromophore combinations in the composition, chromophores which cannot normally be activated by an activating light (such as a blue light from an LED) can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when photoactivated in the presence of molecular oxygen, however it has a low quantum yield in terms of emitted fluorescent light. Rose Bengal has a peak absorption around 540 nm and so is normally activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y which transfers some of its energy to Rose Bengal as well as emitting some energy as fluorescence.

(b) Gelling Agent

The present disclosure provides biophotonic topical compositions that comprise at least a first chromophore and a gelling agent, wherein the gelling agent provides a barrier such that the chromophore(s) of the biophotonic topical compositions are substantially not in contact with the target tissue.

As used herein, "leaching" means the release of one or more components of a biophotonic composition (e.g., the chromophore(s)) from the composition to the surrounding environment such as for example the wound site or into the tissue being treated with the composition). Therefore, the gelling agent present in the biophotonic compositions of the present disclosure renders the compositions substantially resistant to leaching such that the chromophore(s) or photosensitive agent(s) of the biophotonic topical compositions are not in substantial contact with the target tissue.

In certain embodiments, the biophotonic topical composition allows less than 30%, 25%, 20%, 15%, 10%, 5%, 1%, 0.8%, 0.5% or 0.1%, or essentially none of said chromophore content to leach out of the biophotonic composition.

In some embodiments, the biophotonic composition limits leaching of the first chromophore such that less than 15% of total chromophore amount can leach out into tissue during a treatment time in which the composition is topically applied onto tissue and illuminated with light. In some embodiments, the biophotonic composition limits leaching of the first chromophore such that less than 30%, 25%, 20%, 15%, 10%, 5%, 1%, 0.8%, 0.5% or 0.1% or essentially 0% of total chromophore amount can leach out into tissue during a treatment time in which the composition is topically applied onto tissue and illuminated with light. In some embodiments, the treatment time is at least about 5 minutes, at least about 10 minutes, at least about 15 minutes, at least about 20 minutes, at least about 25 minutes or at least about 30 minutes.

The extent of chromophore leaching out of the biophotonic composition and into the surrounding environment may be assessed using various methods known in the art, including but not limited to, the tests described in the Examples.

In some embodiments, leaching is determined by placing the biophotonic composition in contact with an aqueous solution through a porous membrane for a period of time corresponding to a desired treatment time. The extent of chromophore leaching can then be assessed visually, for example, by noting a color change of the aqueous solution, or quantitatively, for example, by using a spectrophotometer to measure the absorption of the solution. In some embodiments, a biophotonic composition of the present disclosure allows less than 30%, 25%, 20%, 15%, 10%, 5%, 1%, 0.8%, 0.5% or 0.1% or essentially 0% of the total chromophore amount to leach out of the biophotonic composition as through a porous membrane into an aqueous solution when the biophotonic composition is placed in contact with the aqueous solution through the porous membrane for a time corresponding to a desired treatment time. In certain embodiments, the time corresponding to a treatment time is at least about 5 minutes, at least about 10 minutes, 15 minutes, 20 minutes, 25 minutes or 30 minutes.

In some embodiments, staining is determined by visually assessing whether the biophotonic composition colorizes white test paper saturated with 70% by volume ethanol/30% by volume water solution placed in contact with the biophotonic composition for a period of time corresponding to a desired treatment time. In some embodiments, a biophotonic composition of the present disclosure does not visually colorize white test paper saturated with a 70% by volume ethanol/30% by volume water solution placed in contact with the biophotonic composition under atmospheric pressure for a time corresponding to a desired treatment time. In certain embodiments, the time corresponding to a treatment time is at least about 5 minutes, at least about 10 minutes, 15 minutes, 20 minutes, 25 minutes or 30 minutes.

A gelling agent for use according to the present disclosure may comprise any ingredient suitable for use in a topical biophotonic formulation as described herein. The gelling agent according to various embodiments of the present disclosure may include, but not limited to, polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); and polyvinylamines.

The gelling agent according to certain embodiments of the present disclosure may include a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or 100,000, or 1,000,000) and/or cross-linked polyacrylic acid polymer. In some embodiments, the polymer is a polyacrylic acid polymer and has a viscosity in the range of about 15,000-100,000, 15,000-90,000, 15,000-80,000, 20,000-80,000, 20,000-70,000, 20,000-40,000 cP. In certain embodiment, the polymer is a high molecular weight, and/or cross-linked polyacrylic acid polymer, where the polyacrylic acid polymer has a viscosity in the range of about 15,000-80,000 cP.

In some embodiments, the gelling agent comprises a carbomer. Carbomers are synthetic high molecular weight polymer of acrylic acid that are crosslinked with either allylsucrose or allylethers of pentaerythritol having a molecular weight of about $3\times10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994)) and Durrani (Pharmaceutical Res. (Supp.) 8:S-135 (1991)), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In certain embodiments, the carbomer is Carbopol® 980 NF, ETD 2020 NF, Ultrez 10 NF, Ultrez 21 or 1382 Polymer, 1342 NF, 940 NF.

In certain embodiments, the gelling agent comprises a hygroscopic material. The hygroscopic material may include, but is not limited to, glucosamine, glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate).

The one or more gelling agents can be selected according to their ability to prevent leaching. For example, gelling agents which can increase the viscosity of the biophotonic composition can be selected. In some embodiments, the viscosity of the biophotonic composition is 15,000-100,000, 15,000-90,000, 15,000-80,000, 20,000-80,000, 20,000-70,000, 20,000-40,000 cP. A composition with sufficiently high viscosity parameters can prevent or limit the leaching of chromophores from the composition. Gelling agents which include lipids or other coating agents which can coat the chromophores can also be used to limit or prevent leaching. Alternatively or in addition to the aforesaid, gelling agents which are hygroscopic and/or hydrophilic may be used for their water attracting properties, which may also prevent or limit leaching of the chromophore.

Viscosity of the biophotonic compositions of the present disclosure may be measured using a cone/plate viscometer (Wells-Brookfield). A CP-51 cone may be used and viscosity is measured at a speed of 2 rpm and making sure that the torque is >10%. Spindle must rotate at least 5 times before a viscosity reading is taken.

The biophotonic composition of the present disclosure may be further encapsulated. e.g., in a membrane. Such a membrane may be transparent, and/or substantially, or fully impermeable. The membrane may be impermeable to liquid but permeable to gases such as air. In certain embodiments, the composition may form a membrane that encapsulates the chromophore(s) of the biophotonic topical composition, where the membrane may be substantially impermeable to liquid and/or gas. In certain embodiments, the biophotonic composition is a liquid encapsulated by a membrane, wherein the membrane is sufficiently resistant to chromophore leaching such that less than 15% of the total chromophore amount leaches out of the encapsulated composition. The membrane may be formed of one or more lipidic agents.

(c) Oxygen-Releasing Agents

According to certain embodiments, the compositions of the present disclosure may optionally further comprise one or more additional components, such as oxygen-releasing agents. For instance, the biophotonic topical composition of the present disclosure may optionally comprise oxygen-releasing agents as a source of oxygen. Peroxide compounds are oxygen-releasing agents that contain the peroxy group (R—O—O—R), which is a chainlike structure containing two oxygen atoms, each of which is bonded to the other and a radical or some element.

When a biophotonic composition of the present disclosure comprising an oxygen-releasing agent is illuminated with light, the chromophore(s) are excited to a higher energy state. When the chromophore(s)' electrons return to a lower energy state, they emit photons with a lower energy level, thus causing the emission of light of a longer wavelength (Stokes' shift). In the proper environment, some of this energy release is transferred to oxygen or the reactive hydrogen peroxide and causes the formation of oxygen radicals, such as singlet oxygen. The singlet oxygen and other reactive oxygen species generated by the activation of the biophotonic composition are thought to operate in a hormetic fashion. That is, a health beneficial effect that is brought about by the low exposure to a normally toxic stimuli (e.g. reactive oxygen), by stimulating and modulating stress response pathways in cells of the targeted tissues. Endogenous response to exogenous generated free radicals (reactive oxygen species) is modulated in increased defense capacity against the exogenous free radicals and induces acceleration of healing and regenerative processes. Furthermore, activation of the composition can also produce an antibacterial effect. The extreme sensitivity of bacteria to exposure to free radicals makes the composition of the present disclosure a de facto bactericidal composition.

As stated above, the generation of oxygen species by the composition in some embodiments is accompanied by the micro-bubbling which can contribute to debridement or dislodging of biofilm at the site of application. This can allow for the improved penetration of the activating and/or fluorescence light to the treatment site for example to deactivate bacterial colonies leading to their reduction in number.

Suitable oxygen-releasing agents that may be included in the composition include, but are not limited to:

Hydrogen peroxide ($H_2O_2$) is the starting material to prepare organic peroxides. $H_2O_2$ is a powerful oxygen-releasing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is from about 0.1% to about 6%.

Urea hydrogen peroxide (also known as urea peroxide, carbamide peroxide or percarbamide) is soluble in water and contains approximately 35% hydrogen peroxide. Carbamide peroxide for use in this composition can be used as a gel, for example with 16% carbamide peroxide that represents 5.6% hydrogen peroxide, or 12% carbamide peroxide. A suitable range of concentration over which urea peroxide can be used in the present composition is from about 0.3% to about 16%. Urea peroxide breaks down to urea and hydrogen peroxide in a slow-release fashion that can be accelerated with heat or photochemical reactions. The released urea [carbamide, $(NH_2)CO_2$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which is toxic. A suitable range of concentration over which benzoyl peroxide can be used in the present composition is from about 2.5% to about 5%.

Specific oxygen-releasing agents that that are preferably used in the materials or methods of this disclosure include, but are not limited to hydrogen peroxide, carbamide peroxide, or benzoyl peroxide. Inclusion of other forms of peroxides (e.g. organic or inorganic peroxides) should be avoided due to their increased toxicity and their unpredictable reaction with the photodynamic energy transfer. Oxygen-releasing agents can be provided in powder, liquid or gel form. Alternatively, the oxygen-releasing agents may also be applied to the tissue site separately to the composition. Alternatively, the composition may include an amount of oxygen-releasing agent, which is augmented by the separate application of oxygen-releasing agents to the treatment site.

In the compositions and methods of the present disclosure, additional components may optionally be included, or used in combination with the biophotonic compositions as described herein. Such additional components include, but are not limited to, healing factors, growth factors, antimicrobials, wrinkle fillers (e.g. botox, hyaluronic acid or polylactic acid), collagens, anti-virals, anti-fungals, antibiotics, drugs, and/or agents that promote collagen synthesis. These additional components may be applied to the wound, skin or mucosa in a topical fashion, prior to, at the same time of, and/or after topical application of the biophotonic composition of the present disclosure, and may also be systemically administered. Suitable healing factors, antimicrobials, collagens, and/or agents that promote collagen synthesis are discussed below:

(d) Healing Factors

Healing factors comprise compounds that promote or enhance the healing or regenerative process of the tissues on the application site of the composition. During the photo-activation of the composition of the present disclosure, there is an increase of the absorption of molecules at the treatment site by the skin, wound or the mucosa. An augmentation in the blood flow at the site of treatment is observed for an extent period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Studies have shown hyaluronic acid appearing in the early stages of healing to physically create room for white blood cells that mediate the immune response. It is used in the synthesis of biological scaffolds for wound healing applications and in wrinkle treatment. A suitable range of concentration over which hyaluronic acid can be used in the present composition is from about 0.001% to about 3%.

Glucosamine: is one of the most abundant monosaccharides in human tissues and a precursor in the biological synthesis of glycosilated proteins and lipids. It is commonly used in the treatment of osteoarthritis. The common form of glucosamine used is its sulfate salt. Glucosamine shows a number of effects including an anti-inflammatory activity, stimulation of the synthesis of proteoglycans and the synthesis of proteolytic enzymes. A suitable range of concentration over which glucosamine can be used in the present composition is from about 0.01% to about 3%.

Allantoin: is a diureide of glyosilic acid. It has keratolytic effect, increases the water content of the extracellular matrix, enhances the desquamation of the upper layers of dead (apoptotic) skin cells, and promotes skin proliferation and wound healing.

Also, saffron can act as both a chromophore and a healing factor. Other healing agents can also be included such as growth factors.

(e) Antimicrobials

Antimicrobials kill microbes or inhibit their growth or accumulation. Exemplary antimicrobials (or antimicrobial agent) are recited in U.S. Patent Application Publications 20040009227 and 20110081530. Suitable antimicrobials for use in the methods of the present disclosure include, but not limited to, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol-; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to; methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2.4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the tradename Triclosan®; 2,2'-methylene bis-(3,4,6-trichlorophenol); 2,2'-methylene bis-(4-chloro-6-bromophenol); bis-(2-hydroxy-3,5-dichlorop-henyl) sulphide; and bis-(2-hydroxy-5-chlorobenzyl)sulphide.

Specific benzoie esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Specific thazolines that can be used in the disclosure include, but are not limited to that sold under the tradename Micro-Check®; and 2-n-octyl-4-isothiazolin-3-one, which is sold under the tradename Vinyzene® IT-3000 DIDP.

Specific trichloromethylthioimides that can be used in the disclosure include, but are not limited to: N-(trichloromethylthio)phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the disclosure include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; eucalyptus; vervain; peppermint; gum benzoin; basil; fennel; fir; balsam; menthol; ocmea origanuin; hydastis; carradensis; Berberidaceac daceae; Ratanhiae longa; and Curcuma longa. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide, citronellic acid; curcumin; nerolidol; and geraniol.

Specific metal salts that can be used in the disclosure include, but are not limited to, salts of metals in groups 3a-5a, 3b-7b, and 8 of the periodic table. Specific examples of metal salts include, but are not limited to, salts of; aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. An example of the metal-ion based antimicrobial agent is sold under the tradename HealthShield®, and is manufactured by HealthShield Technology, Wakefield, Mass. [give other examples here e.g. smith and nephew]

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as that sold under the tradename Octopirox-®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435: 4,625,026; 4,736,467; 4,855,139; 5,069,907; 5,091,102;

5,639,464; 5,853,883; 5,854,147; 5,894.042; and 5,919,554, and U.S. Pat. Appl. Publ. Nos. 20040009227 and 20110081530.

(f) Collagens and Agents that Promote Collagen Synthesis

Collagen is a fibrous protein produced in dermal fibroblast cells and forming 70% of the dermis. Collagen is responsible for the smoothing and firming of the skin. Therefore, when the synthesis of collagen is reduced, skin aging will occur, and so the firming and smoothing of the skin will be rapidly reduced. As a result, the skin will be flaccid and wrinkled. On the other hand, when metabolism of collagen is activated by the stimulation of collagen synthesis in the skin, the components of dermal matrices will be increased, leading to effects, such as wrinkle improvement, firmness improvement and skin strengthening. Thus, collagens and agents that promote collagen synthesis may also be useful in the present disclosure. Agents that promote collagen synthesis (i.e., pro-collagen synthesis agents) include amino acids, peptides, proteins, lipids, small chemical molecules, natural products and extracts from natural products.

For instance, it was discovered that intake of vitamin C, iron, and collagen can effectively increase the amount of collagen in skin or bone. See, e.g., U.S. Patent Application Publication 20090069217. Examples of the vitamin C include an ascorbic acid derivative such as L-ascorbic acid or sodium L-ascorbate, an ascorbic acid preparation obtained by coating ascorbic acid with an emulsifier or the like, and a mixture containing two or more of those vitamin Cs at an arbitrary rate. In addition, natural products containing vitamin C such as acerola and lemon may also be used. Examples of the iron preparation include: an inorganic iron such as ferrous sulfate, sodium ferrous citrate, or ferric pyrophosphate; an organic iron such as heme iron, ferritin iron, or lactoferrin iron; and a mixture containing two or more of those irons at an arbitrary rate. In addition, natural products containing iron such as spinach or liver may also be used. Moreover, examples of the collagen include: an extract obtained by treating bone, skin, or the like of a mammal such as bovine or swine with an acid or alkaline; a peptide obtained by hydrolyzing the extract with a protease such as pepsine, trypsin, or chymotrypsin; and a mixture containing two or more of those collagens at an arbitrary rate. Collagens extracted from plant sources may also be used.

Additional pro-collagen synthesis agents are described, for example, in U.S. Pat. Nos. 7,598,291, 7,722,904, 6,203, 805, 5,529,769, etc, and U.S. Patent Application Publications 20060247313, 20080108681, 20110130459, 20090325885, 20110086060, etc.

(4) Methods of Use

The biophotonic compositions of the present disclosure have numerous uses. Without being bound by theory, the biophotonic compositions of the present disclosure may promote wound healing or tissue repair. The biophotonic compositions of the present disclosure may also be used to treat a skin disorder. The biophotonic compositions of the present disclosure may also be used to treat acne. The biophotonic compositions of the present disclosure may also be used for skin rejuvenation. The biophotonic compositions of the present disclosure may also be used for treating acute inflammation. Therefore, it is an objective of the present disclosure to provide a method for providing biophotonic therapy to a wound, where the method promotes wound healing. It is also an objective of the present disclosure to provide a method for providing biophotonic therapy to a skin tissue afflicted with acne, wherein the method is used to treat acne. It is also an objective of the present disclosure to provide a method for providing biophotonic therapy to a skin tissue afflicted with a skin disorder, wherein the method is used to treat the skin disorder. It is also an objective of the present disclosure to provide a method for providing biophotonic therapy to skin tissue, wherein the method is used for promoting skin rejuvenation.

In certain embodiments, the present disclosure provides a method for providing a biophotonic therapy to a wound, the method comprising: applying (e.g., by topical application) a biophotonic composition of the present disclosure to a site of a wound, and illuminating the biophotonic composition with light having a wavelength that overlaps with an absorption spectrum of the chromophore(s) of the biophotonic composition.

In one aspect, the present disclosure provides a method for providing biophotonic therapy to a wound, comprising: topically applying a biophotonic composition comprising a first chromophore; and illuminating said biophotonic composition with light having a wavelength that overlaps with an absorption spectrum of the first chromophore; wherein the biophotonic composition is substantially resistant to leaching such that it limits leaching of the chromophore into the tissue during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the wound or tissue during treatment.

In another aspect, the present disclosure provides a method for treating a wound or providing biophotonic therapy to a wound, comprising: topically applying a biophotonic composition comprising a first chromophore and a gelling agent to a site of a wound; and illuminating said biophotonic composition with light having a wavelength that overlaps with an absorption spectrum of the first chromophore; wherein the gelling agent blocks substantial leaching of the chromophores into the site of a wound during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the wound or tissue during treatment.

In yet another aspect, the present disclosure provides a method for promoting skin rejuvenation. In certain embodiments, the present disclosure provides a method for providing skin rejuvenation, the method comprising: applying (e.g., by topical application) a biophotonic composition of the present disclosure to the skin, and illuminating the biophotonic composition with light having a wavelength that overlaps with an absorption spectrum of the chromophore(s) of the biophotonic composition.

In other embodiments, the present disclosure provides a method for promoting skin rejuvenation comprising: topically applying a biophotonic composition comprising a first chromophore to skin; and illuminating said biophotonic composition with light having a wavelength that overlaps with an absorption spectrum of the first chromophore; wherein the biophotonic composition is substantially resistant to leaching such that it limits leaching of the chromophore into the skin during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the wound or tissue during treatment.

In another aspect, the present disclosure provides a method for promoting skin rejuvenation, comprising: topically applying a biophotonic composition comprising a first chromophore and a gelling agent to skin; and illuminating said biophotonic composition with light having a wavelength that overlaps with an absorption spectrum of the first chromophore; wherein the biophotonic composition is substantially resistant to leaching such that it blocks substantial leaching of the chromophores into the skin during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the skin during treatment.

In yet another aspect, the present disclosure to provide a method for providing biophotonic therapy to a target skin tissue afflicted with a skin disorder. In certain embodiments, the present disclosure provides a method for providing a biophotonic therapy to a target skin tissue, the method comprising: applying (e.g., by topical application) a biophotonic composition of the present disclosure to a target skin tissue, and illuminating the biophotonic composition with light having a wavelength that overlaps with an absorption spectrum of the chromophore(s) of the biophotonic composition.

In other embodiments, the present disclosure provides a method for treating a skin disorder, comprising: topically applying a biophotonic composition to a target skin tissue afflicted with the skin disorder, wherein the biophotonic composition comprises a first chromophore; and illuminating said biophotonic composition with light having a wavelength that overlaps with an absorption spectrum of the first chromophore; wherein the biophotonic composition is substantially resistant to leaching such that it limits leaching of the chromophore into the skin during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the skin during treatment.

In another aspect, the present disclosure provides a method for treating a skin disorder, comprising: topically applying a biophotonic composition comprising a first chromophore and a gelling agent to skin afflicted with the skin disorder; and illuminating said biophotonic composition with light having a wavelength that overlaps with an absorption spectrum of the first chromophore; wherein the biophotonic composition is substantially resistant to leaching such that it blocks substantial leaching of the chromophores into the skin during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the skin during treatment.

In yet another aspect, the present disclosure to provide a method for providing biophotonic therapy to a target skin tissue afflicted with acne. In certain embodiments, the present disclosure provides a method for providing a biophotonic therapy to a target skin tissue afflicted with acne, the method comprising: applying (e.g., by topical application) a biophotonic composition of the present disclosure to a target skin tissue, and illuminating the biophotonic composition with light having a wavelength that overlaps with an absorption spectrum of the chromophore(s) of the biophotonic composition.

In other embodiments, the present disclosure provides a method for treating acne, comprising: topically applying a biophotonic composition to a target skin tissue afflicted with acne, wherein the biophotonic composition comprises a first chromophore; illuminating said biophotonic composition with light having a wavelength that overlaps with an absorption spectrum of the first chromophore; wherein the biophotonic composition is substantially resistant to leaching such that it limits leaching of the chromophore into tissue during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the tissue during treatment.

In another aspect, the present disclosure provides a method for treating acne, comprising: topically applying a biophotonic composition comprising a first chromophore to skin afflicted with acne; and illuminating said biophotonic composition with light having a wavelength that overlaps with an absorption spectrum of the first chromophore; wherein the biophotonic composition is substantially resistant to leaching such that it blocks substantial leaching of the chromophores into the skin during treatment. In some embodiments, less than 30%, 25%, 20%, 15%, 1%, 5%, 1%, 0.8%, 0.5% or 0.1% or essentially 0% of the total chromophore amount leaches out of the biophotonic composition into the wound or tissue during treatment.

In other embodiments, the present disclosure provides a method for treating acute inflammation, comprising: topically applying a biophotonic composition to a target skin tissue with acute inflammation, wherein the biophotonic composition comprises a first chromophore, illuminating said biophotonic composition with light having a wavelength that overlaps with an absorption spectrum of the first chromophore; wherein the biophotonic composition is substantially resistant to leaching such that it limits leaching of the chromophore into tissue during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the tissue during treatment.

In another aspect, the present disclosure provides a method for treating acute inflammation, comprising: topically applying a biophotonic composition comprising a first chromophore to skin afflicted with acute inflammation; and illuminating said biophotonic composition with light having a wavelength that overlaps with an absorption spectrum of the first chromophore; wherein the biophotonic composition is substantially resistant to leaching such that it blocks substantial leaching of the chromophores into the skin during treatment. In some embodiments, less than 30%, 25%, 20%, 15%, 10%, 5%, 1%, 0.8%, 0.5% or 0.1% or essentially 0% of the total chromophore amount leaches out of the biophotonic composition into the wound or tissue during treatment.

The biophotonic compositions suitable for use in the methods of the present disclosure may be selected from any of the embodiments of the biophotonic compositions described above. For instance, the biophotonic compositions useful in the method of the present disclosure may comprise a first chromophore that undergoes at least partial photobleaching upon application of light. The first chromophore may absorb at a wavelength of about 200-800 nm, 200-700 nm, 200-600 nm or 200-500 nm. In one embodiment, the first chromophore absorbs at a wavelength of about 200-600 nm. In some embodiments, the first chromophore absorbs light at a wavelength of about 200-300 nm, 250-350 nm, 300-400 nm, 350-450 nm, 400-500 nm, 450-650 nm, 600-700 nm, 650-750 nm or 700-800 nm. In other examples, suitable biophotonic compositions for the methods of the present disclosure may further comprise at least one additional chromophore (e.g., a second chromophore). The absorption spectrum of the second chromophore overlaps at least about 80%, 50%, 40%, 30%, or 20% with the emission spectrum of the first chromophore. In some embodiments, the first chromophore has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second chromophore.

Illumination of the biophotonic composition with light may cause a transfer of energy from the first chromophore to the second chromophore. Subsequently, the second chromophore may emit energy as fluorescence and/or generate reactive oxygen species. In certain embodiments of the methods the present disclosure, energy transfer caused by the application of light is not accompanied by concomitant generation of heat, or does not result in tissue damage.

The biophotonic compositions useful for the present methods comprise a gelling agent. The gelling agent may include, but is not limited to, lipids such as glycerin, glycols such as propylene glycol, hyaluronic acid, glucosamine sulfate, cellulose derivatives (hydroxypropyl methylcellulose, hydroxyethyl cellulose, hydroxypropyl cellulose, methylcellulose and the like), noncellulose polysaccharides (galactomannans, guar gum, carob gum, gum arabic, sterculia gum, agar, alginates and the like) and acrylic acid polymers.

When the method involves a biophotonic composition having at least two chromophores, the first chromophore is present in an amount of about 0.01-40% per weight of the composition, and the second chromophore is present in an amount of about 0.001-40% per weight of the composition. In certain embodiments, the first chromophore is present in an amount of about 0.01-1%, 0.5-2%, 1-50%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the total weight per weight of chromophore or combination of chromophores may be in the amount of about 0.01-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In the methods of the present disclosure, any source of actinic light can be used. Any type of halogen, LED or plasma arc lamp or laser may be suitable. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a GreenLight™ laser) is used. In another embodiment, sunlight may be used. In yet another embodiment, a LED photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm. Furthermore, the source of actinic light should have a suitable power density. Suitable power density for non-collimated light sources (LED, halogen or plasma lamps) are in the range from about 1 mW/cm$^2$ to about 200 mW/cm$^2$. Suitable power density for laser light sources are in the range from about 0.5 mW/cm$^2$ to about 0.8 mW/cm.

In some embodiments of the methods of the present disclosure, the light has an energy at the subject's skin, wound or mucosa surface of between about 1 mW/cm$^2$ and about 500 mW/cm$^2$, 1-300 mW/cm$^2$, or 1-200 mW/cm$^2$, wherein the energy applied depends at least on the condition being treated, the wavelength of the light, the distance of the subject's skin from the light source, and the thickness of the biophotonic composition. In certain embodiments, the light at the subject's skin is between about 1-40 mW/cm$^2$, or 20-60 mW/cm$^2$, or 40-80 mW/cm$^2$, or 60-100 mW/cm$^2$, or 80-120 mW/cm$^2$, or 100-140 mW/cm$^2$, or 120-160 mW/cm$^2$, or 140-180 mW/cm$^2$, or 160-200 mW/cm$^2$, or 110-240 mW/cm$^2$, or 110-150 mW/cm$^2$, or 190-240 mW/cm$^2$.

In some embodiments, a mobile device can be used to activate embodiments of the biophotonic composition of the present disclosure, wherein the mobile device can emit light having an emission spectra which overlaps an absorption spectra of the chromophore in the biophotonic composition. The mobile device can have a display screen through which the light is emitted and/or the mobile device can emit light from a flashlight which can photoactivate the biophotonic composition.

In some embodiments, a display screen on a television or a computer monitor can be used to activate the biophotonic composition, wherein the display screen can emit light having an emission spectra which overlaps an absorption spectra of a photoactive agent in the photoactivatable composition.

In certain embodiments, the first and/or the second chromophore (when present) can be photoactivated by ambient light which may originate from the sun or other light sources. Ambient light can be considered to be a general illumination that comes from all directions in a room that has no visible source. In certain embodiments, the first and/or the second chromophore (when present) can be photoactivated by light in the visible range of the electromagnetic spectrum. Exposure times to ambient light may be longer than that to direct light.

In certain embodiments, different sources of light can be used to activate the biophotonic compositions, such as a combination of ambient light and direct LED light.

The duration of the exposure to actinic light required will be dependent on the surface of the treated area, the type of lesion, trauma or injury that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In one embodiment, the time of exposure to actinic light of the tissue, skin or wound on which the biophotonic composition has been applied is a period between 1 minute and 5 minutes. In another embodiment, the time of exposure to actinic light of the tissue, skin or wound on which the biophotonic composition has been applied is a period between 1 minute and 5 minutes. In some other embodiments, the biophotonic composition is illuminated for a period between 1 minute and 3 minutes. In certain embodiments, light is applied for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 20-30 minutes. In yet another embodiment, the source of actinic light is in continuous motion over the treated area for the appropriate time of exposure. In yet another embodiment, multiple applications of the biophotonic composition and actinic light are performed. In some embodiments, the tissue, skin or wound is exposed to actinic light at least two, three, four, five or six times. In some embodiments, a fresh application of the biophotonic composition is applied before exposure to actinic light.

In the methods of the present disclosure, the biophotonic composition may be optionally removed from the site of treatment following application of light. In certain embodiments, the biophotonic composition is left on the treatment site for more than 30 minutes, more than one hour, more than 2 hours, more than 3 hours. It can be illuminated with ambient light. To prevent drying, the composition can be covered with a transparent or translucent cover such as a polymer film, or an opaque cover which can be removed before illumination.

(5) Wounds and Wound Healing

The biophotonic compositions and methods of the present disclosure may be used to treat wounds and promote wound healing. Wounds that may be treated by the biophotonic compositions and methods of the present disclosure include, for example, injuries to the skin and subcutaneous tissue initiated in different ways (e.g., pressure ulcers from extended bed rest, wounds induced by trauma, wounds induced by conditions such as periodontitis) and with varying characteristics. In certain embodiments, the present disclosure provides biophotonic compositions and methods for treating and/or promoting the healing of, for example, burns, incisions, excisions, lacerations, abrasions, puncture or penetrating wounds, surgical wounds, contusions, hematomas, crushing injuries, sores and ulcers.

Biophotonic compositions and methods of the present disclosure may be used to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology:pressure ulcers, neuropathic (diabetic foot) ulcers and vascular (venous or arterial) ulcers.

In certain other embodiments, the present disclosure provides biophotonic compositions and methods for treating and/or promoting healing, Grade I-IV ulcers. In certain embodiments, the application provides compositions suitable for use with Grade II ulcers in particular. Ulcers may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

For example, the present disclosure provides biophotonic compositions and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In certain embodiments, compositions and methods of treating a chronic wound are provided here in, where the chronic wound is characterized by diabetic foot ulcers and/or ulcerations due to neurologic and/or vascular complications of diabetes.

In other examples, the present disclosure provides biophotonic compositions and methods for treating and/or promoting healing of a pressure ulcer. Pressure ulcer includes bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turns red, becomes painful and can become necrotic. If untreated, the skin breaks open and can become infected. An ulcer sore is therefore a skin ulcer that occurs in an area of the skin that is under pressure from e.g. lying in bed, sitting in a wheelchair, and/or wearing a cast for a prolonged period of time. Pressure ulcer can occur when a person is bedridden, unconscious, unable to sense pain, or immobile. Pressure ulcer often occur in boney prominences of the body such as the buttocks area (on the sacrum or iliac crest), or on the heels of foot.

In other examples, the present disclosure provides biophotonic compositions and methods for treating and/or promoting healing of acute wounds.

Additional types of wound that can be treated by the biophotonic compositions and methods of the present disclosure include those disclosed by U.S. Pat. Appl. Publ. No. 20090220450, which is incorporated herein by reference.

Wound healing in adult tissues is a complicated reparative process. For example, the healing process for skin involves the recruitment of a variety of specialized cells to the site of the wound, extracellular matrix and basement membrane deposition, angiogenesis, selective protease activity and re-epithelialization.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic compositions and methods of the present disclosure promote the wound healing by promoting the formation of substantially uniform epithelialization; promoting collagen synthesis; promoting controlled contraction; and/or by reducing the formation of scar tissue. In certain embodiments, the biophotonic compositions and methods of the present disclosure may promote wound healing by promoting the formation of substantially uniform epithelialization. In some embodiments, the biophotonic compositions and methods of the present disclosure promote collagen synthesis. In some other embodiments, the biophotonic compositions and methods of the present disclosure promote controlled contraction. In certain embodiments, the biophotonic compositions and methods of the present disclosure promote wound healing, for example, by reducing the formation of scar tissue or by speeding up the wound closure process. In certain embodiments, the biophotonic compositions and methods of the present disclosure promote wound healing, for example, by reducing inflammation. In certain embodiments, the biophotonic composition can be used following wound closure to optimize scar revision. In this case, the biophotonic composition may be applied at regular intervals such as once a week, or at an interval deemed appropriate by the physician.

The biophotonic composition may be soaked into a woven or non-woven material or a sponge and applied as a wound dressing. A light source, such as LEDs or waveguides, may be provided within or adjacent the wound dressing or the composition to illuminate the composition. The waveguides can be optical fibres which can transmit light, not only from their ends, but also from their body. For example, made of polycarbonate or polymethylmethacrylate.

Adjunct therapies which may be topical or systemic such as antibiotic treatment may also be used. Negative pressure assisted wound closure can also be used to assist wound closure and/or to remove the composition.

(6) Acne and Acne Scars

The biophotonic compositions and methods of the present disclosure may be used to treat acne. As used herein. "acne" means a disorder of the skin caused by inflammation of skin glands or hair follicles. The biophotonic compositions and methods of the disclosure can be used to treat acne at early pre-emergent stages or later stages where lesions from acne are visible. Mild, moderate and severe acne can be treated with embodiments of the biophotonic compositions and methods. Early pre-emergent stages of acne usually begin with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the biophotonic compositions and methods of the present disclosure can be used to treat one or more of skin irritation, pitting, development of scars, comedones, inflammatory papules, cysts, hyperkeratinazation, and thickening and hardening of sebum associated with acne.

The composition may be soaked into or applied to a woven or non-woven material or a sponge and applied as a mask to body parts such as the face, body, arms, legs etc. A light source, such as LEDs or waveguides, may be provided within or adjacent the mask or the composition to illuminate the composition. The waveguides can be optical fibres which can transmit light, not only from their ends, but also from their body. For example, made of polycarbonate or polymethylmethacrylate.

The biophotonic compositions and methods of the present disclosure may be used to treat various types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, and nodulocystic acne.

(7) Skin Aging and Rejuvenation

The dermis is the second layer of skin, containing the structural elements of the skin, the connective tissue. There are various types of connective tissue with different functions. Elastin fibers give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

The aging of skin comes with significant physiological changes to the skin. The generation of new skin cells slows down, and the epidermal ridges of the dermal-epidermal junction flatten out. While the number of elastin fibers increases, their structure and coherence decrease. Also the amount of collagen and the thickness of the dermis decrease with the ageing of the skin.

Collagen is a major component of the skin's extracellular matrix, providing a structural framework. During the aging process, the decrease of collagen synthesis and insolubilization of collagen fibers contribute to a thinning of the dermis and loss of the skin's biomechanical properties.

The physiological changes to the skin result in noticeable aging symptoms often referred to as chronological-, intrinsic- and photo-ageing. The skin becomes drier, roughness and scaling increase, the appearance becomes duller, and most obviously fine lines and wrinkles appear. Other symptoms or signs of skin aging include, but are not limited to, thinning and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, a blotchy complexion.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of α-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Recently another type of wrinkles generally referred to as expression wrinkles, got general recognition. These wrinkles require loss of resilience, particularly in the dermis, because of which the skin is no longer able to resume its original state when facial muscles which produce facial expressions exert stress on the skin, resulting in expression wrinkles.

The compositions and methods of the present disclosure promote skin rejuvenation. In certain embodiments, the compositions and methods of the present disclosure promote collagen synthesis. In certain other embodiments, the compositions and methods of the present disclosure may reduce, diminish, retard or even reverse one or more signs of skin aging including, but not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. In certain embodiments, the compositions and methods of the present disclosure may induce a reduction in pore size, enhance sculpturing of skin subsections, and/or enhance skin translucence.

(8) Skin Disorders

The biophotonic compositions and methods of the present disclosure may be used to treat skin disorders that include, but are not limited to, erythema, telangiectasia, actinic telangiectasia, psoriasis, skin cancer, pemphigus, sunburn, dermatitis, eczema, rashes, impetigo, lichen simplex chronicus, rhinophyma, perioral dermatitis, pseudofolliculitis barbae, drug eruptions, erythema multiforme, erythema nodosum, granuloma annulare, actinic keratosis, purpura, alopecia areata, aphthous stomatitis, drug eruptions, dry skin, chapping, xerosis, ichthyosis vulgaris, fungal infections, parasitic infection, herpes simplex, intertrigo, keloids, keratoses, milia, moluscum contagiosum, pityriasis rosea, pruritus, urticaria, and vascular tumors and malformations. Dermatitis includes contact dermatitis, atopic dermatitis, seborrheic dermatitis, nummular dermatitis, generalized exfoliative dermatitis, and statis dermatitis. Skin cancers include melanoma, basal cell carcinoma, and squamous cell carcinoma.

Some skin disorders present various symptoms including redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors. Accordingly, the biophotonic compositions and methods of the present disclosure can be used to treat redness, flushing, burning, scaling, pimples, papules, pustules, comedones, macules, nodules, vesicles, blisters, telangiectasia, spider veins, sores, surface irritations or pain, itching, acute inflammation, red, purple, or blue patches or discolorations, moles, and/or tumors. Acute inflammation can present itself as pain, heat, redness, swelling and loss of function. It includes those seen in allergic reactions such as insect bites e.g.; mosquito, bees, wasps, poison ivy, post-ablative treatment.

The composition may be soaked into or applied to a woven or non-woven material or a sponge and applied as a mask to body parts to treat skin disorders. A light source, such as LEDs or waveguides, may be provided within or adjacent the mask or the composition to illuminate the composition. The waveguides can be optical fibres which can transmit light, not only from their ends, but also from their body. For example, made of polycarbonate or polymethylmethacrylate.

(9) Kits

The present disclosure also provides kits for preparing and/or applying any of the compositions of the present disclosure. The kit may include a biophotonic topical composition comprising at least a first chromophore in a gelling agent. The composition may include an oxygen-releasing agent present in amount about 0.01%-40%, 0.01%-1.0%, 0.5%-10.0%, 5%-15%, 10%-20%, 15%-25%, 20%-30%, 15.0%-25%, 20%-30%, 25%-35%, or 30%-40% by weight to weight of the composition. The chromophore may be present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In embodiments where the composition comprises more than one chromophore, the first chromophore may be present in an amount of about 0.01-40% per weight of the composition, and a second chromophore may be present in an amount of about 0.01-40% per weight of the composition. In certain embodiments, the first chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the amount of chromophore or combination of chromophores may be in the amount of about 0.05-40.05% per weight of the composition. In certain embodiments, the amount of chromophore or combination of chromophores may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In some embodiments, the kit includes more than one composition, for example, a first and a second composition. The first composition may include the oxygen-releasing agent and the second composition may include the first chromophore in the gelling agent. The first chromophore may have an emission wavelength between about 400 nm and about 570 nm. The oxygen-releasing agent may be present in the first composition in an amount of about 0.01%-1.0%, 0.5%-10.0%, 5%-15%, 10%-20%, 15%-25%, 20%-30%, 15.0%-25%, 20%-30%, 25%-35%, 30%-40% or 35%-45% by weight to weight of the first composition. The chromophore may be present in the second composition in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In embodiments where the second composition comprises more than one chromophore, the first chromophore may be present in an amount of about 0.01-40% per weight of the second composition, and a second chromophore may be present in an amount of about 0.0001-40% per weight of the second composition. In certain embodiments, the first chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-309%, 27.5-32.5%, 30-35%, 32.5-37.5%, or 35-40% per weight of the second composition. In certain embodiments, the second chromophore is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the second composition. In certain embodiments, the amount of chromophore or combination of chromophores may be in the amount of about 0.05-40.05% per weight of the second composition. In certain embodiments, the amount of chromophore or combination of chromophores may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the second chromophore.

In some other embodiments, the first composition may comprise the first chromophore in a liquid or as a powder, and the second composition may comprise a gelling composition for thickening the first composition. The oxygen-releasing agent may be contained in the second composition or in a third composition in the kit. In some embodiments, the kit includes containers comprising the compositions of the present disclosure. In some embodiments, the kit includes a first container comprising a first composition that includes the oxygen-releasing agent, and a second container comprising a second composition that includes at least one chromophore. The containers may be light impermeable, air-tight and/or leak resistant. Exemplary containers include, but are not limited to, syringes, vials, or pouches. The first and second compositions may be included within the same container but separated from one another until a user mixes the compositions. For example, the container may be a dual-chamber syringe where the contents of the chambers mix on expulsion of the compositions from the chambers. In another example, the pouch may include two chambers separated by a frangible membrane. In another example, one component may be contained in a syringe and injectable into a container comprising the second component.

The biophotonic composition may also be provided in a container comprising one or more chambers for holding one or more components of the biophotonic composition, and an outlet in communication with the one or more chambers for discharging the biophotonic composition from the container. In one embodiment, discharging the biophotonic compositions causes the components of the composition to mix to form a biophotonic composition which has less than 15% leaching properties.

In other embodiments, the kit comprises a systemic or topical drug for augmenting the treatment of the composition. For example, the kit may include a systemic or topical antibiotic or hormone treatment for acne treatment or wound healing.

Written instructions on how to use the biophotonic composition in accordance with the present disclosure may be included in the kit, or may be included on or associated with the containers comprising the compositions of the present disclosure.

In certain embodiments, the kit may comprise a further component which is a dressing. The dressing may be a porous or semi-porous structure for receiving the biophotonic composition. The dressing may comprise woven or non-woven fibrous materials.

In certain embodiments of the kit, the kit may further comprise a light source such as a portable light with a wavelength appropriate to activate the chromophore in the biophotonic composition. The portable light may be battery operated or re-chargeable.

In certain embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

Example 1

Figure 6A:
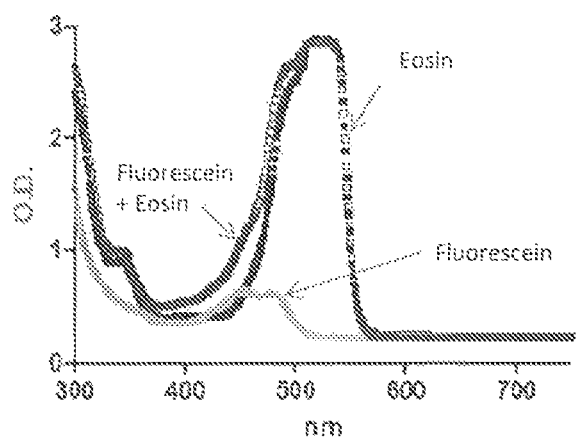
FIGS. 6a and 6b are absorbance and emission spectra, respectively, of a composition according to certain embodiments of the present disclosure which includes Eosin and Fluorescein in a gel (Example 1).
Figure 6B:
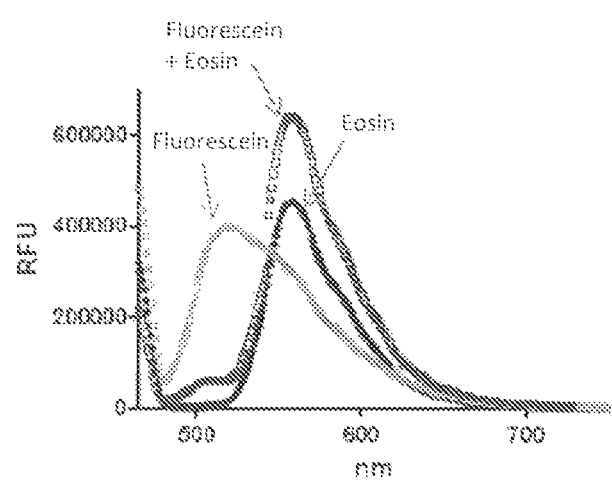

The photodynamic properties of (i) Fluorescein sodium salt at about 0.09 mg/mL, (ii) Eosin Y at about 0.305 mg/mL, and (iii) a mixture of Fluorescein sodium salt at about 0.09 mg/mL and Eosin Y at about 0.305 mg/mL in a gel according to an embodiment of the present disclosure (comprising about 12% carbamide peroxide), were evaluated. A flexstation 384 II spectrometer was used with the following parameters: mode fluorescence, excitation 460 nm, emission spectra 465-750 nm. The absorption and emission spectra are shown in FIGS. 6a and 6b which indicate an energy transfer between the chromophores in the combination.

Example 2

Figure 7A:
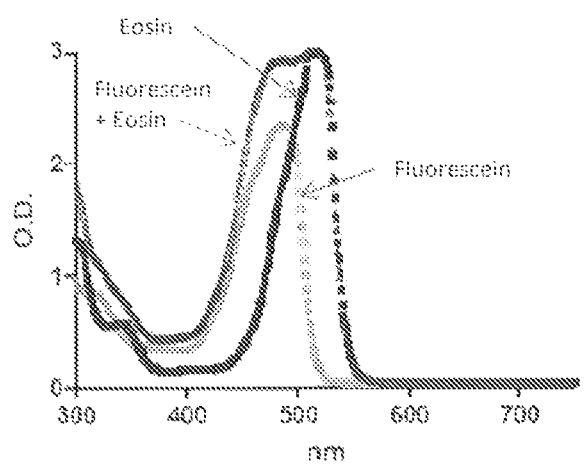
FIGS. 7a and 7b are absorbance and emission spectra, respectively, of a composition according to certain embodiments of the present disclosure which includes Eosin and Fluorescein in an aqueous solution (Example 2).
Figure 7B:
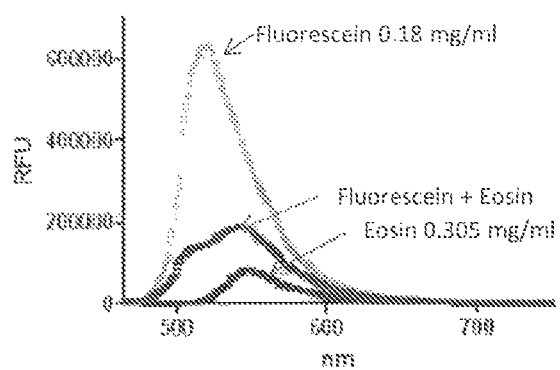

The photodynamic properties of (i) Fluorescein sodium salt at 0.18 mg/mL final concentration, (ii) Eosin Y at about 0.305 mg/mL, and (iii) a mixture of Fluorescein sodium salt at about 0.18 mg/mL and Eosin Y at about 0.305 mg/mL in an aqueous solution were evaluated. A flexstation 384 II spectrometer was used with the following parameters: mode fluorescence, excitation 460 nm, emission spectra 465-750 nm. The absorption and emission spectra are shown in FIGS. 7a and 7b which indicate an energy transfer between the chromophores in the combination.

Example 3

Figure 8A:
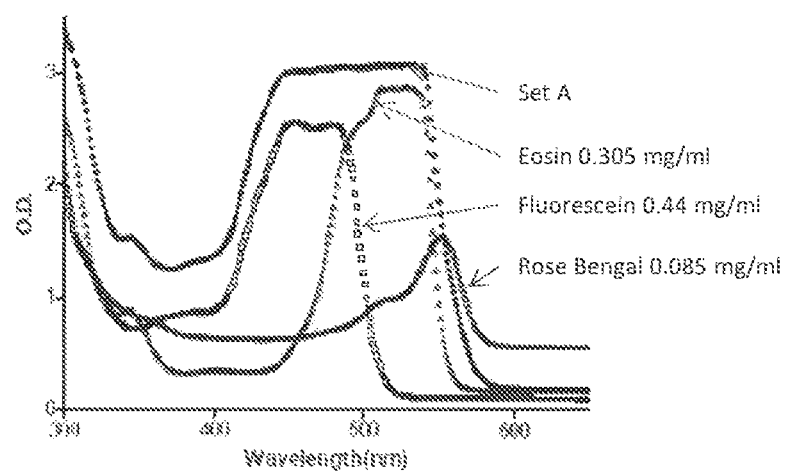
FIGS. 8a and 8b are absorbance and emission spectra, respectively, of a composition according to certain embodiments of the present disclosure which includes Eosin, Fluorescein and Rose Bengal in a gel (Example 3).
Figure 8B:
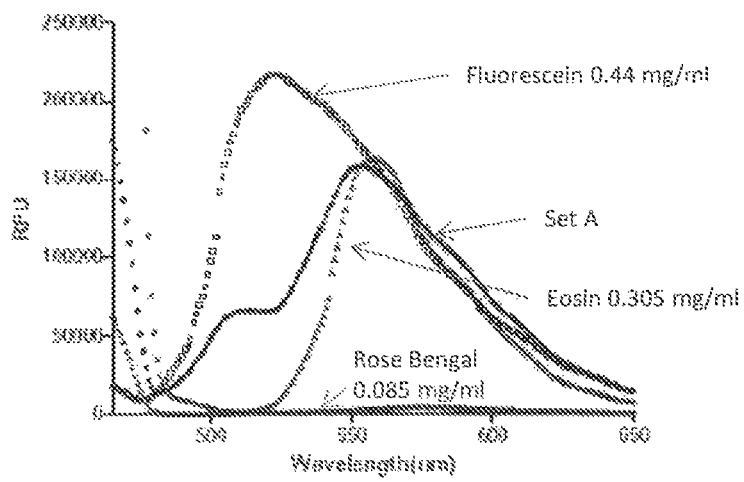

The photodynamic properties of (i) Rose Bengal at about 0.085 mg/mL, (ii) Fluorescein sodium salt at about 0.44 mg/mL final concentration, (ii) Eosin Y at about 0.305 mg/mL, and (iii) a mixture of (i), (ii) and (iii) in a gel comprising about 12% carbamide peroxide (Set A), according to an embodiment of the invention, were evaluated. A flexstation 384 II spectrometer was used with the following parameters: mode fluorescence, excitation 460 nm, emission spectra 465-750 nm. The absorbance and emission spectra are shown in FIGS. 8a and 8b which indicate an energy transfer between the chromophores in the chromophore combination.

Example 4

Figure 9A:
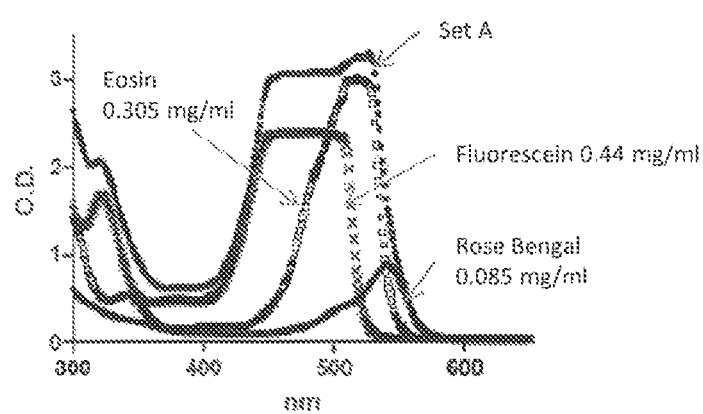
FIGS. 9a and 9b are absorbance and emission spectra, respectively, of a composition according to certain embodiments of the present disclosure which includes Eosin and Fluorescein in an aqueous solution (Example 4).
Figure 9B:
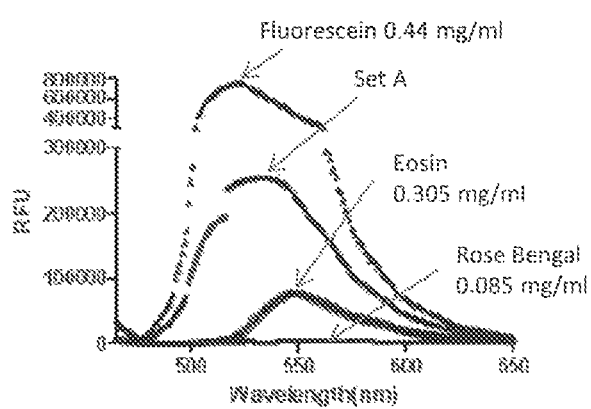
Figure 10:
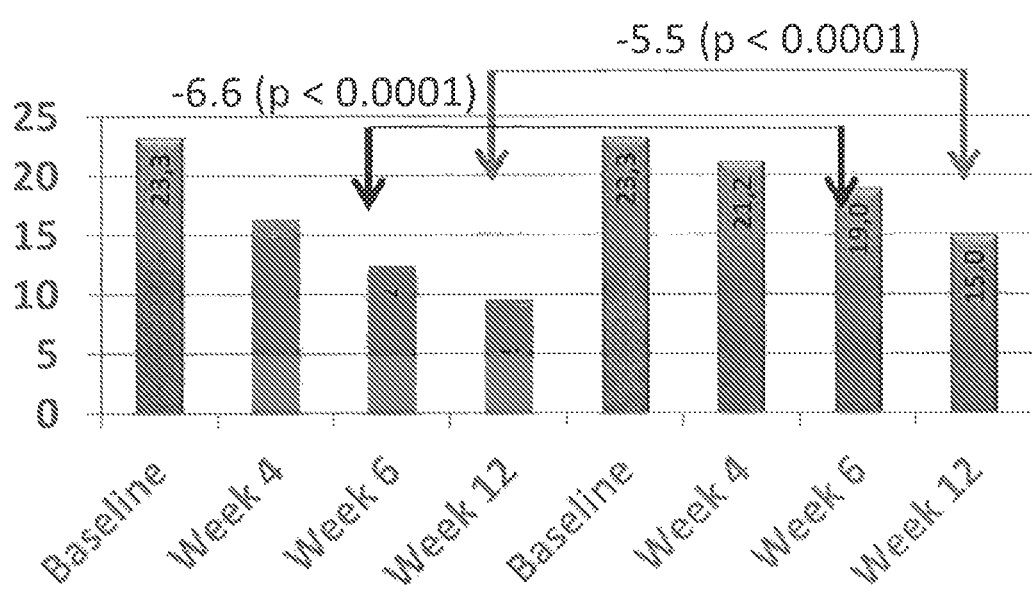
FIG. 10 illustrates a summary of inflammatory lesion count and absolute changes by hemiface (Example 5).

The photodynamic properties of (i) Rose Bengal at about 0.085 mg/mL, (ii) Fluorescein sodium salt at about 0.44 mg/mL final concentration, (ii) Eosin Y at about 0.305 mg/mL, and (iii) a mixture of (i), (ii) and (iii) in an aqueous solution (Set A), were evaluated. A flexstation 384 II spectrometer was used with the following parameters: mode fluorescence, excitation 460 nm, emission spectra 465-750 nm. The absorbance and emission spectra are shown in FIGS. 9a and 9b which indicate an energy transfer between the chromophores in the chromophore combination, in the absence of an oxygen-releasing agent.

Energy transfer was also seen between: Eosin Y and Rose Bengal; Phloxine B and EosinY; Phloxine B, EosinY and Fluorescein, amongst other combinations. It is to be reasonably inferred that energy transfer can also occur in biophotonic compositions of the present disclosure.

Example 5

A randomized, split-face clinical trial of 12 weeks was performed on 90 patients (ages 14-30) having moderate to severe facial acne. Moderate facial acne was defined as having "an Investigator's Global Assessment (IGA) of 3 with 20-40 inflammatory lesions and no more than 1 nodule". Severe facial acne was defined as having "an IGA of 4 with more than 40 inflammatory lesions with the presence of more than 2 nodules and/or presence of sever erythema and inflammatory scarring type lesion". For each patient, one randomly selected side of the face was treated twice a week for 6 weeks with a biophotonic composition comprising Eosin Y and an oxygen-releasing agent, and exposed to light from an LED source (peak wavelength range 400-470 nm) for about 5 minutes. Other hemiface remained untreated for the 6 week period. Both the treated and untreated sides of the face were evaluated after 12 weeks. Results are presented in Tables 1-5 below. The treatment was well tolerated by the patients and there were no serious adverse events. 80% of patients completed the study with no adverse events reported.

At week 4, there was a 30% reduction in inflammatory lesions (including papules, pustules and nodules) for the treated group compared to 9.0% reduction for untreated. At week 6, the reduction was 46.8% for treated and 18.4% for untreated, and at week 12, the reduction was 59.2% for treated and 35.6% for untreated.

TABLE 1

Total reduction from baseline in IGA at week 12 of more than or equal to 2 grades and less than 2 grades tor treated and untreated hemifaces.

| | Total reduction from baseline in IGA at week 12 | |
| --- | --- | --- |
| | Treated (n = 89) | Untreated (n = 89) |
| ≥2 grades | 46 (51.7%)* | 16 (18.0%) |
| <2 grades | 43 (48.3%)* | 73 (82.0%) |

*P value < 0.0001

TABLE 2

Total reduction from baseline in IGA at week 12 of more than or equal to 1 grade and less than 1 grade for treated and untreated hemifaces.

| | Total reduction from baseline in IGA at week 12 | | Total reduction from baseline in IGA at week 6 | |
| --- | --- | --- | --- | --- |
| (n = 89) | Treated | Untreated | Treated | Untreated |
| ≥1 grade | 79 (88.8%)* | 62 (69.7%) | 71 (79.8%)+ | 40 (44.9%) |
| <1 grade | 10 (11.2%)* | 27 (30.3%) | 18 (20.2%)+ | 49 (55.1%) |

*P value < 0.0001
+P value < 0.0001

TABLE 3

Total reduction from baseline in IGA at weeks 6 and 12 to grade 0 and grade 1 and grades 2, 3 or 4 for treated and untreated hemifaces.

| (n = 89) | Total reduction from baseline in IGA at week 12 | | Total reduction from baseline in IGA at week 6 | |
|---|---|---|---|---|
| | Treated | Untreated | Treated | Untreated |
| To Grade 0 or 1 | 29 (32.6%)* | 10 (11.2%) | 16 (18.0%)+ | 6 (6.7%) |
| To Grade 2, 3 or 4 | (67.4%)* | 79 (88.8%) | 73 (82.0%)+ | 83 (93.2%) |

\*P value < 0.0001
+P value < 0.0213

TABLE 4

Proportion of patients showing at least 40% reduction from baseline in inflammatory lesion count (includes papules, pustules and nodules) at weeks 6 and 12 for treated and untreated hemifaces.

| | Total reduction from baseline in inflammatory lesion count at week 12 | | Total reduction from baseline in inflammatory lesion count at week 6 | |
|---|---|---|---|---|
| | Treated (n = 87) | Untreated (n = 87) | Treated (n = 87) | Untreated (n = 87) |
| ≥40% | 71 (81.6%)* | 40 (46.0%) | 56 (64.4%)+ | 27 (31.0%) |
| <40% | (18.4%)* | 47 (54.0%) | 31 (35.6%)+ | 60 (69.0%) |

\*P value < 0.0001
+P value < 0.0001

TABLE 5

Summary of inflammatory lesion count and absolute changes by hemiface.

| Inflammatory Lesion Count* | | Treated | | Untreated | | Difference (Treated − Untreated) | |
|---|---|---|---|---|---|---|---|
| | | Lesion Count | Change | Lesion Count | Change | Change (Absolute) | Change |
| Baseline | n | 90 | | 90 | | 90 | |
| | Mean | 23.0 | | 23.3 | | −0.3 | |
| | (SD) | (13.79) | | (15.41) | | (7.10) | |
| Week 4 | n | 87 | 87 | 87 | 87 | 87 | 87 |
| | Mean | 16.3 | −6.9 | 21.2 | −2.3 | −4.9 | −4.6 |
| | (SD) | (10.82) | (6.55) | (14.39) | (5.44) | (7.58) | (7.74) |
| Week 6 | n | 87 | 87 | 87 | 87 | 87 | 87 |
| | Mean | 12.4 | −10.9 | 19.0 | −4.5 | −6.6 | −6.3 |
| | (SD) | (8.35) | (8.85) | (13.92) | (7.24) | (8.34) | (9.35) |
| | p value | | | | | <0.0001 | <0.0001 |
| Week 12 | n | 87 | 87 | 87 | 87 | 87 | 87 |
| | Mean | 9.5 | −13.7 | 15.0 | −8.5 | −5.5 | −5.2 |
| | (SD) | (7.10) | (11.52) | (11.33) | (11.04) | (7.37) | (9.05) |
| | p value | | | | | <0.0001 | <0.0001 |

*Includes papules, pustules and nodules

Figure 14:
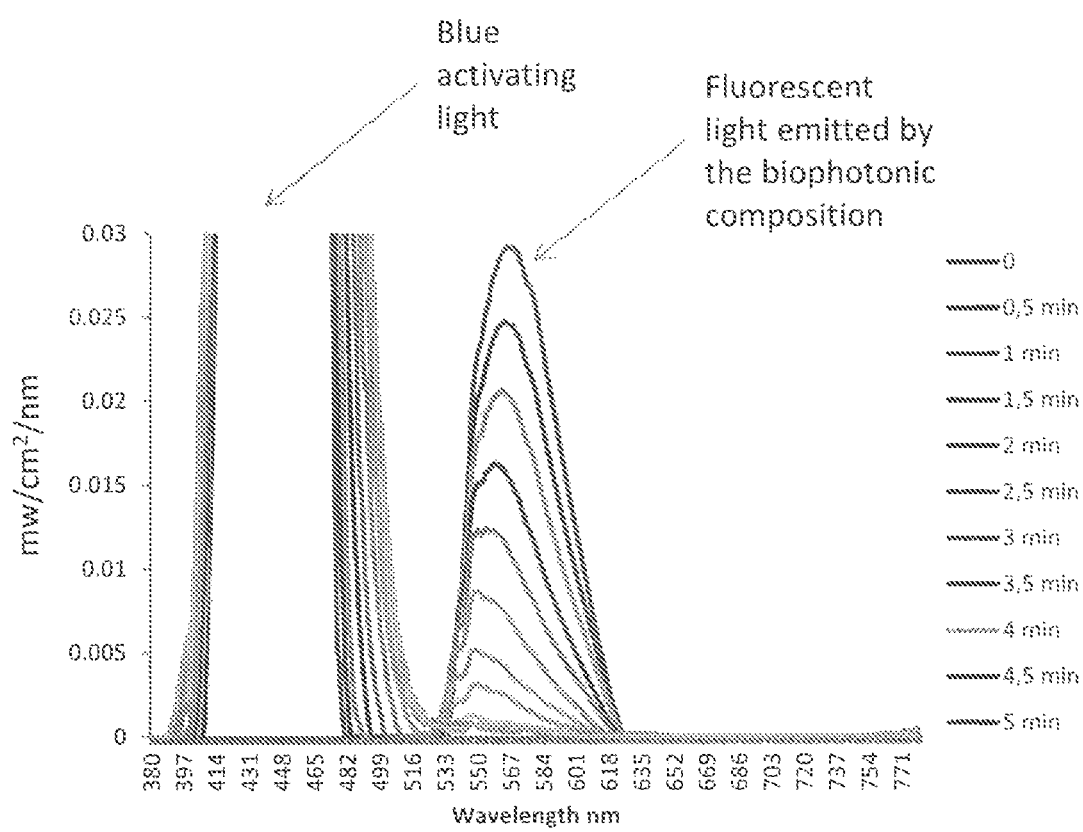
FIG. 14 is an emission spectrum showing the intensity over time of the light being emitted from the biophotonic composition tested in Example 5.

FIG. 14 is an emission spectrum showing the intensity over time of the light being emitted from the biophotonic composition.

Example 6—Leaching Test Using Polycarbonate Membrane

Figure 5:
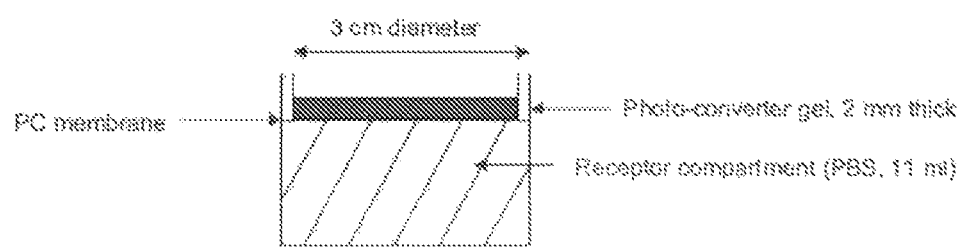
FIG. 5 depicts the experimental setup of an in vitro release test for evaluating leaching of the chromophore(s) of the biophotonic compositions (Example 6).

FIG. 5 depicts an experimental setup of an in vitro release test for evaluating leaching of the chromophore(s) or other components (e.g., oxygen releasing agents) from the biophotonic compositions of the present disclosure. In this in vitro test, a 2 mm thick layer of the biophotonic composition is applied on the surface of a 3 cm diameter polycarbonate (PC) membrane with pore size of 3 μm. It will be appreciated that other membranes with different pore sizes can also be used. The membrane is in direct contact with phosphate saline buffer (PBS) or PBS containing 4% bovine serum albumin (PBS/BSA) contained in a closed compartment (i.e., the receptor compartment). The biophotonic composition is then illuminated with an activating light for an appropriate period of time (e.g., 5 min) at an appropriate distance (e.g. 5 cm from the light source). Samples (100 μl×2) are then taken from the receptor compartment at different time points (e.g., at 5, 10, 20, and 30 min), and evaluated for concentration of the chromophore(s) or any other components of the biophotonic composition using spectrophotometry or any other suitable method.

For example, when the chromophore being tested is eosin, a wavelength of 517 nm (absorbance) may be used. The concentration of the chromophore may then be calculated based on the chromophore standards of known concentration prepared in PBS or PBS/BSA and measured at the same time. Moreover, the presence of peroxide (i.e., an indicator of the oxygen releasing agents) may be assessed using peroxide test sticks (e.g. Quantofix Peroxide 25, Sigma Aldrich).

Table 9 summarizes leaching data for different biophotonic compositions according to the present disclosure. The amount of hydrogen peroxide found in the receptor compartment was very low for all compositions in Table 9. The detection method of chromophore by spectrophotometry can measure the chromophore concentration from 0.2 μg/ml. The release of chromophores increased overtime but was less than 15% even after 30 minutes incubation which is longer than a treatment time according to embodiments of the present disclosure.

TABLE 9

Percentage of chromophores released from biophotonic compositions according to embodiments of the present disclosure, with time of incubation.

| | Percentage chromophore released into receptor compartment from composition with time of incubation (n = 3) | | | |
|---|---|---|---|---|
| | 5 mins | 10 mins | 20 mins | 30 mins |
| Eosin Y (0.011%) in a carbamide gel (glycerine, propylene glycol, carbopol polymer, urea peroxide) | Not detectable | Not detectable | 0.75 | 0.78 |
| Fluorescein (0.2%) in a carbamide gel | 2.71 | 4.85 | 4.72 | 4.84 |
| Rose Bengal (0.2%) in a carbamide gel | 2.39 | 3.32 | 5.26 | 5.21 |
| Rose Bengal (0.1%) + Fluorescein (0.1%) in a carbamide gel | 2.91 | 5.21 | 8.48 | 8.43 |
| Phloxin B (0.2%) in a carbamide gel | 0.54 | 2.39 | 4.62 | 4.50 |
| Eosin Y (0.2%) in a carbamide gel | 2.77 | 2.72 | 6.56 | 9.08 |
| Phloxin B (0.1%) and Fluorescein (0.1%) in a carbamide gel | 2.28 | 4.49 | 7.56 | 11.02 |
| Phloxin B (0.1%) and Rose Bengal (0.1%) in a carbamide gel | 2.41 | 2.36 | 5.14 | 4.90 |
| Eosin Y (0.1%) + Phloxin B (0.1%) in a carbamide gel | 3.84 | 6.25 | 10.08 | 12.00 |
| Eosin Y (0.1%) + Rose Bengal (0.1%) a carbamide gel | 3.04 | 4.28 | 6.63 | 8.12 |
| Eosin Y (0.1%) + Fluorescein (0.1%) in a carbamide gel | 2.96 | 3.99 | 5.78 | 7.58 |
| Phloxin B (0.1%) + Eosin Y (0.1%) in a carbopol polymer gel | 1.00 | 2.3 | 4.48 | 5.80 |
| Eosin Y (0.2%) in a carbopol polymer gel including urea peroxide | 6.78 | 8.2 | 14.38 | 17.89 |
| Phloxin B (0.1%) + Eosin Y (0.1%) in a 5% gelatin gel | 0.51 | 0.25 | 1.79 | 3.14 |
| Rose Bengal (0.1%) + Eosin Y (0.1%) in a 5% gelatin gel | 0 | 0.39 | 1.39 | 2.15 |

Example 7—Angiogenic Potential of the Biophotonic Composition of the Disclosure

A human skin model was developed to assess the angiogenic potential of the biophotonic composition of the present disclosure. Briefly, a biophotonic composition a biophotonic composition comprising Eosin Y and Erythrosine was placed on top of a human skin model containing fibroblasts and keratinocytes. The skin model and the composition were separated by a nylon mesh of 20 micron pore size. The composition was then irradiated with blue light ('activating light') for 5 minutes at a distance of 5 cm from the light source. The activating light consisted of light emitted from an LED lamp having an average peak wavelength of about 400-470 nm, and a power intensity measured at 10 cm of 7.7 J/cm$^2$ to 11.5 J/cm$^2$. Upon illumination with the activating light, the biophotonic composition emitted fluorescent light (FIG. 4). Since the biophotonic composition was in limited contact with the cells, the fibroblasts and keratinocytes were exposed mainly to the activating light and the fluorescent light emitted from the biophotonic composition. Conditioned media from the treated human 3D skin model were then applied to human aortic endothelial cells previously plated in matrigel. The formation of tubes by endothelial cells was observed and monitored by microscopy after 24 hours. The conditioned medium from 3D skin models treated with light illumination induced endothelial tube formation in vitro, suggesting an indirect effect of the light treatment (blue light and fluorescence) on angiogenesis via the production of factors by fibroblasts and keratinocytes. Plain medium and conditioned medium from untreated skin samples were used as a control, and did not induce endothelial tube formation.

Figure 15:
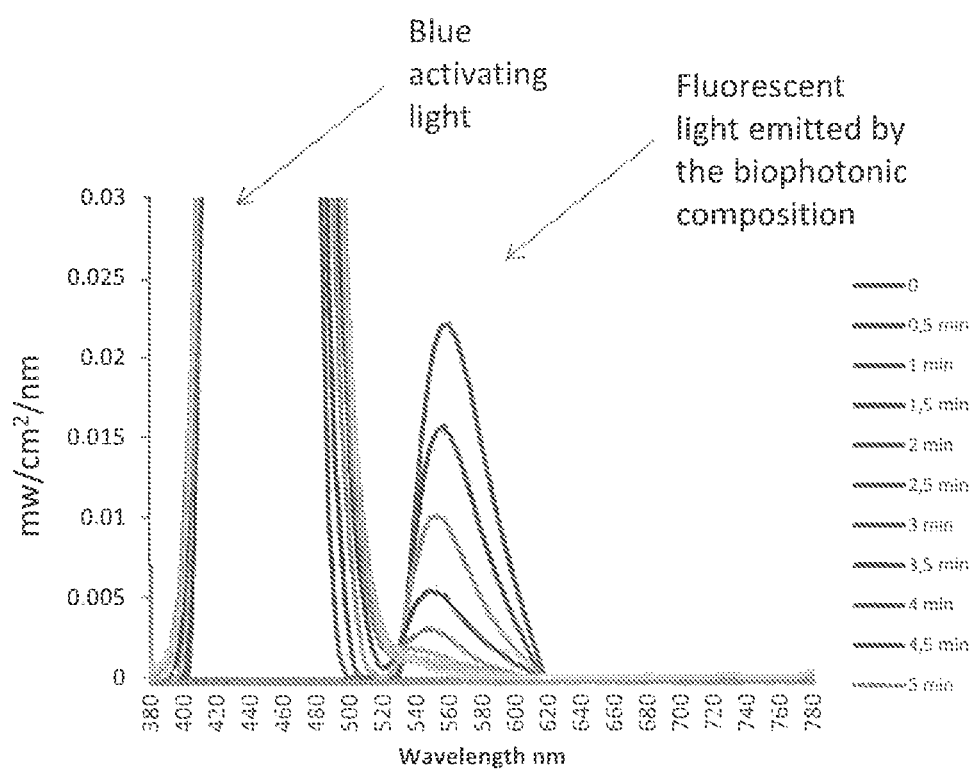
FIG. 15 is an emission spectrum showing the intensity over time of the light being emitted from the biophotonic composition tested in Example 7.

FIG. 15 is an emission spectrum showing the intensity over time of the light being emitted from the biophotonic composition.

Example 8—Protein Secretion and Gene Expression Profiles

Wounded and unwounded 3D human skin models (EpiDermFT, MatTek Corporation) were used to assess the potential of a biophotonic composition of the present disclosure to trigger distinct protein secretion and gene expression profiles. Briefly, a biophotonic composition comprising Eosin and Erythrosine were placed on top of wounded and unwounded 3D human skin models cultured under different conditions (with growth factors, 50% growth factors and no growth factors). The skin models and the composition were separated by a nylon mesh of 20 micron pore size. Each skin model-composition combination was then irradiated with blue light ('activating light') for 5 minutes at a distance of 5 cm from the light source. The activating light consisted of light emitted from an LED lamp having an average peak wavelength of about 440-470 nm, a power density of 60-150 mW/cm2 at 5 cm, and a total intensity after 5 minutes of about 18-39 J/cm2. The controls consisted of 3D skin models not illuminated with light.

Gene expression and protein secretion profiles were measured 24 hours post-light exposure. Cytokine secretion was analyzed by antibody arrays (RayBio Human Cytokine antibody array), gene expression was analyzed by PCR array (PAHS-013A, SABioscience) and cytotoxicity was determined by GAPDH and LDH release. Results (Tables 1 and 2) showed that the light treatment is capable of increasing the level of protein secreted and gene expression involved in the early inflammatory phase of wound healing in wounded skin inserts and in non-starvation conditions. In starvation conditions mimicking chronic wounds, there was no increase in the level of inflammatory protein secreted when compared to the control. Interestingly, the effect of the light treatment on unwounded skin models has a much lower impact at the cellular level than on wounded skin insert, which suggests an effect at the cellular effect level of the light treatment. It seems to accelerate the inflammatory phase of the wound healing process. Due to the lack of other cell types such as macrophages in the 3D skin model, the anti-inflammatory feed-back is absent and may explain the delay in wound closure. Cytotoxicity was not observed in the light treatments.

TABLE 6

List of proteins with statistically significant difference secretion ratio between treated and untreated control at day 3. Two arrows mean that the ratio was over 2 folds.

| | Medium 1X | Medium 0.5X | Medium 0X |
|---|---|---|---|
| Increase | | ENA78 p = 0.04 ↑↑ | Angiogenin p = 0.03 ↑ |
| | | Il-1R4/ST2 p = 0.02 ↑↑ | CXCL16 p = 0.04 ↑ |
| | | MMP3 p = 0.01 ↑↑ | |
| | | MCP-2 p = 0.04 ↑↑ | |
| Decrease | BMP6 p = 0.01 ↓ | BMP6 p = 0.02 ↓ | |
| | TNFα p = 0.005 ↓ | | |

TABLE 7

List of genes with statistically significant difference expression ratio between treated and untreated control during the first 24 hours. Two arrows mean that the ratio was over 2 folds.

| | Medium 1X | Medium 0.5X | Medium 0X |
|---|---|---|---|
| Increase | CTGF p = 0.02 ↑ | CTGF P = 0.04 ↑ | MMP3 p = 0.007 ↑↑ |
| | ITGB3 p = 0.03 ↑ | ITGB3 p = 0.05 ↑ | LAMA1 p = 0.03 ↑ |
| | MMP1 p = 0.03 ↑ | MMP1 p = 0.02 ↑↑ | ITGA2 p = 0.03 ↑ |
| | MMP3 p = 0.01 ↑ | MMP10 p = 0.003 ↑↑ | |
| | THBS1 P = 0.02↑ | MMP3 p = 0.007 ↑↑ | |
| | | MMP8 p = 0.02 ↑↑ | |
| | | THBS1 p = 0.03 ↑ | |
| Decrease | HAS1 p = 0.009 ↓↓ | NCAM1 p = 0.02 ↓↓ | |
| | NCAM1 p = 0.05 ↓↓ | VCAN p = 0.02 ↓ | |
| | VCAM1 p = 0.03 ↓↓ | LAMC1 p = 0.002 ↓ | |
| | COL7A1 p = 0.04 ↓ | COL6A1 p = 0.007 ↓ | |
| | CTNNA1 p = 0.03 ↓ | MMP7 p = 0.003 ↓ | |

Example 9—Collagen Formation in Skin

A randomized, placebo-controlled, single-blinded, split face and single hand study of 32 patients, split into 4 groups (A, B, C and D), assessed the safety and efficacy of treatment once a week for 4 weeks: (A) "light alone"—light, according to an embodiment of the present disclosure, comprising light from an LED source having an average peak wavelength of about 400-490 nm at a power density of less than 150 mW/cm$^2$ for 5 minutes; and a placebo formulation; (B) "light+gel"—light as in (A) plus biophotonic gel according to an embodiment of the present disclosure); (C) "gel alone"—biophotonic gel as in (B) and a sham light (white LED light); and (D) 0.1% retinoic based cream. Skin biopsies were obtained before treatment and 12 weeks after treatment from the treatment site. Histological samples of the skin biopsies were graded by an independent and experienced pathologist blinded to the treatment assignment. The results are presented in Table 8 below and show that the light treatment with and without the biophotonic gel, according to embodiments of the present disclosure, showed a 287% and 400% increase from the baseline, respectively, in collagen clusters as viewed through Gomori Trichome staining, in the treated areas of skin. There were no serious adverse events. There was no reported or observed photosensitivity, inflammation or pain.

TABLE 8

Semi-quantitative histological collagen evaluation

| Treatment | % increase in collagen |
|---|---|
| Photoactivatable composition excited with light having 460 nm peak wavelength | 400 |
| Placebo composition + light having 460 nm peak wavelength | 287 |
| Retinol cream with no light | 189 |
| Placebo composition with white light | 150 |

Example 10—Flap Closure

Figure 11:
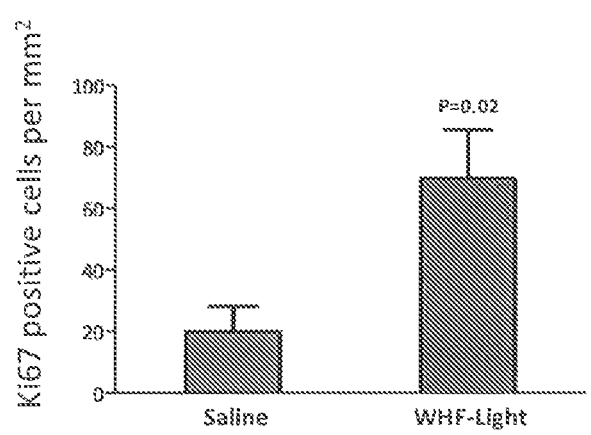
FIG. 11 shows the effect of a biophotonic composition of the disclosure on Ki67 expression (Example 10).

A caudally based rectangular flap was elevated in the back of Wistar rats. A silicone sheet was inserted beneath the skin flap to prevent adhesion and reperfusion of the flap from the underlying tissues. Following flap closure, a biophotonic gel according to an embodiment of the present disclosure (including chromophores and hydroscopic agents) was applied onto the dorsal flap in a thin monolayer (2 mm) and exposed to a light, for 5 minutes, from a LED light source having a peak wavelength of about 440-470 nm and a bandwidth of about 18-23 nm. The biophotonic gel was removed and skin specimens were collected from different areas in the flap for histological analyses nine days post-treatment. The treated group demonstrated a significantly greater number of Ki67-positive-staining events (P=0.02) compared to those in the non-treated group these results, suggesting that the treatment may modulate the proliferation of the cells involved in wound healing (FIG. 11). Following examination by an external pathologist, the treatment group was associated with a significant (P<0.05) decrease in the coagulative necrosis in the epidermis and an increase of the fibrillar stroma (dermis) as compared to the control group.

Example 11—Evaluation of Removal of Biophotonic Composition from Ethanol Soaked Paper Regular white print paper was soaked in 70% ethanol (EtOH). A 2 mm thickness of different embodiment's of biophotonic compositions according to the present disclosure (Table 10) were placed onto the soaked paper and left for 5 minutes. After 5 minutes, the compositions were washed off with 70% EtOH. A composition comprising Eosin (0.017%), silica particles, modified starch, and hydrogen peroxide was also tested.

The results show that biophotonic compositions of the present disclosure including a carbamide gel do not stain white paper. A composition containing Eosin and another hydrophilic polymer (starch) in combination with silica particles did stain the paper.

TABLE 10

Evaluation of removal of biophotonic composition from paper

| Biophotonic composition | Colour of paper after washing |
|---|---|
| Eosin (0.017%), silica particles, modified starch, hydrogen peroxide (included for comparison only). | Orange/red stain on paper observed. |
| Eosin (0.011%) in a urea peroxide, glycerin, propylene glycol, carbopol, hyaluronic acid, glucosamine gel. | Substantially white - no staining observed. |

TABLE 10-continued

Evaluation of removal of biophotonic composition from paper

| Biophotonic composition | Colour of paper after washing |
|---|---|
| Eosin (0.011%) + carbamide peroxide + 1.8% carbopol 940 | Substantially white - no staining observed. |

Example 12—Evaluation of Heat Dissipation During Illumination of a Biophotonic Composition A 3 mm thick layer of a biophotonic composition according to an embodiment of the present disclosure comprising a fluorescent chromophore in a gel according to an embodiment of the present disclosure was applied on the skin of hands of volunteers with different skin types and illuminated for 5 minutes with a blue LED light having a power density of about 50 to 150 mW/cm$^2$ at a distance of 5 cm from the light. A thermometer probe was placed within the composition, at the surface of the skin, and the temperature was monitored in real-time during illumination of the composition. The skin temperature with no composition but the same light illumination was also measured for the same volunteers. The skin types tested were, according to Fitzpatrick classification scales, type III (white skin, sometimes burns and gradually tans), type IV (beige to brown skin, rarely burns and easily tans) and type VI (black skin, never burns, very easily tans). The results are shown in table 7.

TABLE 11

Temperature of skin under biophotonic composition during illumination for 5 minutes compared to temperature skin with no composition and illumination alone

| | Minimum-maximum temperature of skin under composition during 5 mins of illumination/° C. (Average over 5 mins/° C.) | Minimum-maximum temperature of skin without composition during 5 mins, of illumination/° C. (Average over 5 mins/° C.) |
|---|---|---|
| Skin Type III | 26.5-35.1 (32.2) | 28.7-39.1 (36.2) |
| Skin Type IV | 27.6-39.9 (36.1) | 31.4-39.9 (37.0) |
| Skin Type VI | 28.5-39.9 (35.6) | 29.6-40.0 (37.4) |

All skin types with biophotonic composition applied demonstrated a slower temperature increase compared to bare skin (no biophotonic composition), and so the biophotonic composition conferred a buffer effect. After 5 minutes of light illumination, the temperature of the skin under the biophotonic composition for all volunteers reached a maximum of 39.9° C., compared to 40° C. with light alone and bare skin. Overall no pain, burning or discomfort was felt by the volunteers.

Figure 12:
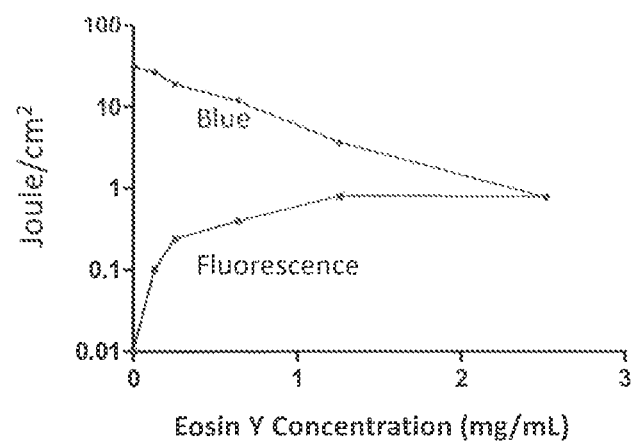
FIG. 12 shows that emitted fluorescence from chromophore in a composition increases rapidly with increasing composition but slows down to a plateau with further concentration increase for Eosin Y (top) and Fluorescein (bottom) (Example 13).
Figure 12:
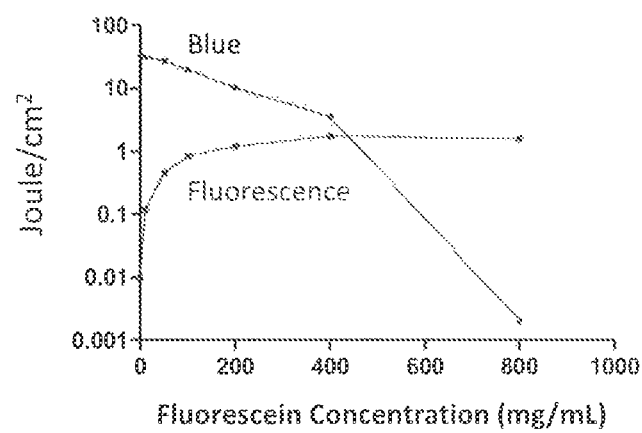

Example 13—Selecting the Concentration of Chromophore in the Biophotonic Composition The fluorescence spectra of biophotonic compositions with different concentrations of chromophores were investigated using a spectrophotometer and an activating blue light. Exemplary fluorescence spectra of Eosin Y and Fluorescein are presented in FIG. 12. It was found that emitted fluorescence from the chromophore increases rapidly with increasing concentration but slows down to a plateau with further concentration increase. Activating light passing through the composition decreases with increasing chromophore composition as more is absorbed by the chromophores. Therefore, the concentration of chromophores in biophotonic compositions of the present disclosure can be selected according to a required ratio and level of activating light and fluorescence treating the tissue based on this example. In some embodiments, it will be after the zone of rapid increase, i.e. between 0.5 and 1 mg/mL for Eosin Y (FIG. 12).

Therefore, concentration can be selected according to required activating light and fluorescence. In some embodiments, it will be after zone of rapid increase, i.e. between 0.5 and 1 mg/mL for Eosin Y (FIG. 12).

Example 14—Eosin and Rose Bengal Act in a Synergistic Manner

The synergy between two chromophores according to various embodiments of the present disclosure was investigated by preparing the following:
1—Eosin Y (0.035%)+Rose Bengal (0.085%) in a 12% carbamide gel)
2—Rose Bengal (0.085%) in a 12% carbamide gel Rose Bengal is known to have a high quantum yield in terms of oxygen production in the presence of oxygen-releasing agents when photoactivated by green light. Eosin Y is known to have a high quantum yield in terms of emitted fluorescent light when photoactivated and can be at least partially activated by blue light when in a gel. Photoactivated Eosin Y does not have a high quantum yield in terms of oxygen production in the presence of oxygen-releasing agents. When Eosin Y and Rose Bengal are combined, it appears that both chromophores are activated by the same blue light as evidenced by FIG. 13.

Figure 13:
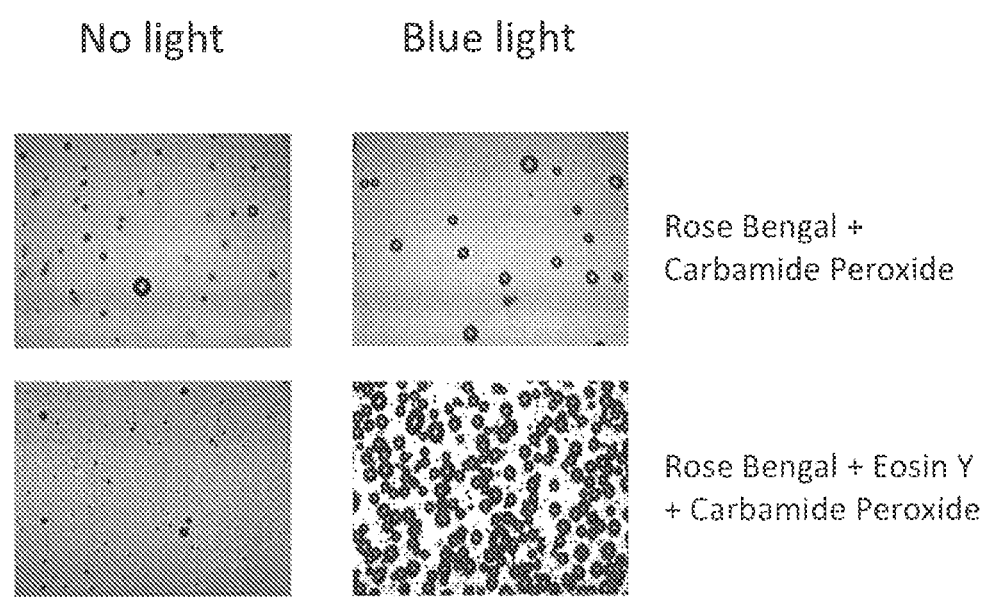
FIG. 13 shows that Eosin and Rose Bengal act in a synergistic manner (Example 14).

FIG. 13, left panel, shows a photograph of the composition when viewed under a light microscope (×250) before exposure to an activating light. Very few bubbles were seen in both compositions. Following illumination with blue light a dramatic increase in bubbles was seen with the composition comprising a combination of Eosin Y and Rose Bengal, but not with the composition comprising Rose Bengal alone. This suggests that there is a transfer of energy from Eosin Y to Rose Bengal leading to the form oxygen species.

What is claimed is:
1. A method for treating a bacterial infection, comprising:
(a) topically applying on an infected tissue an effective amount of a biophotonic composition comprising:
a first chromophore; and
a gelling agent present in the biophotonic composition in an amount sufficient to gel the biophotonic composition to render the biophotonic composition substantially resistant to leaching such that less than 15% by weight of the total chromophore amount leaches out of the biophotonic composition as measured by:
placing a 2 mm thick layer of the biophotonic composition onto a top surface of a 2.4-3 cm diameter polycarbonate membrane with a thickness of 10 microns and a pore size of 3 microns;
contacting a bottom surface of the polycarbonate membrane with a phosphate saline buffer solution contained in a receptor compartment; and
after a treatment time of 5 minutes at room temperature and pressure, measuring the chromophore content in the receptor compartment; and
wherein the first chromophore is dispersed throughout the biophotonic composition; and
wherein the biophotonic composition is photoactivatable and when photoactivated, the biophotonic composition emits light having a wavelength ranging from about 490 nm to about 800 nm; and (b) illuminating said biophotonic composition with light having a wavelength that overlaps with an absorption spectrum of the first chromophore.

2. The method according to claim 1, wherein said biophotonic composition is illuminated for about 1 minute to about 30 minutes, preferably for less than 20 minutes, less than 15 minutes, less than 10 minutes or about 5 minutes.

3. The method according to claim 1, wherein said biophotonic composition is illuminated with visible non-coherent light.

4. The method according to claim 1, wherein the light emitted by the biophotonic composition has a power density of between 0.005 to about 10 mW/cm$^2$.

5. The method according to claim 1, wherein said biophotonic composition is translucent.

6. The method of claim 5, wherein the translucency comprises at least 20%, 30%, 40%, 45%, 50%, 55%, 60%, 65%, 70%, 75%, 85%, 90%, 95% or 100% transmittance of light through a 2 mm thick composition.

7. The method according to claim 1, wherein the first chromophore is selected from the group consisting of Eosin Y, Eosin B, Erythrosin B, Fluorescein, Rose Bengal and Phloxin B.

8. The method according to claim 1, wherein the first chromophore is present in an amount of about 0.001% to about 40% by weight of the total composition.

9. The method according to claim 1, wherein the gelling agent is at least one selected from the group consisting of glycerin, propylene glycol, a high molecular weight cross-linked polyacrylic acid polymer, and a hydrophilic polymer.

10. The method according to claim 1, wherein the gelling agent is a synthetic polymer selected from the group consisting of vinyl polymers, polyoxyethylene-polyoxypropylene copolymers, poly(ethylene oxide), acrylamide polymers and salts thereof.

11. The method according to claim 1, wherein said biophotonic composition further comprises a humectant.

12. The method of claim 11, wherein the humectant is glycerine.

13. The method according to claim 1, wherein said biophotonic composition further comprises a second chromophore.

14. The method according to claim 13, wherein the first chromophore has an emission spectrum that overlaps at least 20% with an absorption spectrum of the second chromophore.

15. The method according to claim 13, wherein the first chromophore is Eosin Y, and the second chromophore is one or more of Fluorescein, Phloxine B or Erythrosine B.

16. The method according to claim 13, wherein the first chromophore is Fluorescein, and the second chromophore is Eosin Y.

17. The method according to claim 1, wherein the biophotonic composition has a viscosity ranging from about 10 000 cP and about 100 000 cP.

18. The method according to claim 1, wherein the biophotonic composition further comprises an oxygen-releasing agent.

19. The method according to claim 18, wherein the oxygen-releasing agent is selected from the group consisting of hydrogen peroxide, carbamide peroxide, benzoyl peroxide, peroxy acid, alkali metal peroxides, alkali metal percarbonates, peroxyacetic acid, and alkali metal perborates.

* * * * *

UNITED STATES PATENT AND TRADEMARK OFFICE
CERTIFICATE OF CORRECTION

PATENT NO. : 11,331,257 B2
APPLICATION NO. : 16/536996
DATED : May 17, 2022
INVENTOR(S) : Remigio Piergallini et al.

It is certified that error appears in the above-identified patent and that said Letters Patent is hereby corrected as shown below:

In the Specification

- In Column 11, Lines 59-62, "...880 at 460 nm. 89% at 460 nm. 90% at 460 nm, 901% at 460 nm, 92% at 460 nm, 93% at 460 nm. 94% at 460 nm, 95% at 460 nm, 96% at 460 nm. 97% at..." should read -- 88% at 460 nm, 89% at 460 nm, 90% at 460 nm, 901% at 460 nm, 92% at 460 nm, 93% at 460 nm, 94% at 460 nm, 95% at 460 nm, 96% at 460 nm, 97% at --

- In Column 12, Lines 32-34, "...wavelength of about 200-300 nm. 250-350 nm. 300-400 nm. 350-450 nm, 400-500 nm. 400-600 nm, 450-650 nm. 600-700 nm, 650-750 nm or 700-800 nm." should read -- wavelength of about 200-300 nm, 250-350 nm, 300-400 nm, 350-450 nm, 400-500 nm, 400-600 nm, 450-650 nm, 600-700 nm, 650-750 nm or 700-800 nm; --

- In Column 18, Line 58, "... solution of Carbopol®) is acidic..." should read -- solution of Carbopol® is acidic --

- In Column 28, Line 15, "... 20%, 15%, 1%, 5%, 1%..." should read -- 20%, 15%, 10%, 5%, 1% --

- In Column 29, Line 28, "... 0.5-2%, 1-50%, 2.5-7.5%..." should read -- 0.5-2%, 1-5%, 2.5-7.5% --

- In Column 37, Line 55, "... 22.5-27.5%, 25-309%, 27.5-32.5%..." should read -- 22.5-27.5%, 25-30%, 27.5-32.5% --

Signed and Sealed this
Ninth Day of May, 2023

Katherine Kelly Vidal
*Director of the United States Patent and Trademark Office*